(12) United States Patent
Bertin et al.

(10) Patent No.: US 9,765,307 B2
(45) Date of Patent: Sep. 19, 2017

(54) CYTOCHROME P450 POLYPEPTIDE WITH INCREASED ENZYME ACTIVITY

(71) Applicant: Sanofi, Paris (FR)

(72) Inventors: Marine Bertin, Paris (FR); Bruno Dumas, Paris (FR)

(73) Assignee: SANOFI, Paris (FR)

( * ) Notice: Subject to any disclaimer, the term of this patent is extended or adjusted under 35 U.S.C. 154(b) by 25 days.

(21) Appl. No.: 14/601,162

(22) Filed: Jan. 20, 2015

(65) Prior Publication Data
US 2015/0225703 A1 Aug. 13, 2015

(30) Foreign Application Priority Data
Jan. 20, 2014 (EP) .................................. 14305071

(51) Int. Cl.
| C12N 9/02 | (2006.01) |
| C12N 15/00 | (2006.01) |
| C12P 21/04 | (2006.01) |
| C12P 21/06 | (2006.01) |
| C12P 33/00 | (2006.01) |
| C07H 21/04 | (2006.01) |

(52) U.S. Cl.
CPC ......... *C12N 9/0079* (2013.01); *C12N 9/0071* (2013.01); *C12P 33/00* (2013.01)

(58) Field of Classification Search
CPC ...... C12N 9/0079; C12N 9/0071; C12P 33/00
See application file for complete search history.

(56) References Cited

U.S. PATENT DOCUMENTS

| 4,861,719 A | 8/1989 | Miller |
| 5,278,056 A | 1/1994 | Bank et al. |
| 5,882,877 A | 3/1999 | Gregory et al. |
| 6,013,516 A | 1/2000 | Verma et al. |
| 6,127,175 A | 10/2000 | Vigne et al. |
| 6,464,998 B1 | 10/2002 | Beuzard et al. |

FOREIGN PATENT DOCUMENTS

| WO | 94/19478 A1 | 9/1994 |
| WO | 95/14785 A1 | 6/1995 |
| WO | 96/22378 A1 | 7/1996 |
| WO | 2012/109326 A2 | 8/2012 |

OTHER PUBLICATIONS

Okuyama. Molecular cloning and nucleotide sequences of cDNA clones of sheep and goat adrenocortical cytochromes P450scc (CYP11A1). J. Steroid Biochem. Mol. Biol. 57:179-185(1996).*
Barg et al. (2005) "Protein and vitamin production in Bacillus megaterium," Ch.11 In; Microbiology Processes and Products. pp. 165-184.
Bleif et al. (Jul. 22, 2011) "A new Bacillus megaterium whole-cell catalyst for the hydroxylation of the pentacyclic triterpene 11-keto-β-boswellic acid (KBA) based on a recombinant cytochrome P450 system," Appl. Microbiol. Biotechnol. 93:1135-1146.
Brady et al. (1984) "New cosmid vectors developed for eukaryotic DNA cloning," Gene. 27(2):223-232.
Database GenBank [Online] (Oct. 18, 2015) "cholesterol side-chain cleavage enzyme, mitochondrial precursor [Sus scrofa]," Accession No. NP_999592.1. Accessible on the Internet at URL: http://www.ncbi.nlm.nih.gov/protein/NP_999592.1. [Last Accessed Jun. 13, 2016].
Database UniProt [Online] (1984) "UniProtKB—P00189 (CP11A_BOVIN)," Accession No. P00189. Accessible on the Internet at URL: http://www.uniprot.org/uniprot/P00189. [Last Accessed Jun. 13, 2016].
Database UniProt [Online] (1985) "UniProtKB—P00257 (ADX_BOVIN)," Accession No. P00257. Accessible on the Internet at URL: http://www.uniprot.org/uniprot/P00257. [Last Accessed Jun. 13, 2016].
Database UniProt [Online] (1987) "UniProtKB—P08165 (ADRO_BOVIN)," Accession No. P08165. Accessible on the Internet at URL: http://www.uniprot.org/uniprot/P08165. [Last Accessed Jun. 13, 2016].
Database UniProt [Online] (2007) "UniProtKB—A3KMX9 (A3KMX9_BOVIN)," Accession No. A3KMX9. Accessible on the Internet at URL: http://www.uniprot.org/uniprot/A3KMX9. [Last Accessed Jun. 13, 2016].
Duport et al. (1998) "Self-sufficient biosynthesis of pregnenolone and progesterone in engineered yeast," Nat. Biotechnol. 16(2):186-189.
Janocha et al. (2011) "Substitution of lysine with glutamic acid at position 193 in bovine CYP11A1 significantly affects protein oligomerization and solubility but not enzymatic activity," Biochim. Biophys. Acta 1814(1):126-131.
Korneli et al. (2013) "Getting the big beast to work—systems biotechnology of Bacillus megaterium for novel high-value proteins," J. Biotechnol. 163:87-96.
Miller et al. (1998) "Early Steps in Androgen Biosynthesis: From Cholesterol to DHEA," Baillieres Clin. Endocrinol. Metab. 12(1):67-81.
Miyaji et al. (1990) "Expression of human lymphotoxin in Namalwa KJM-1 cells adapted to serum-free medium," Cytotechnology. 4(1):39-43.
Miyaji et al. (1990) "Expression of human beta-interferon in Namalwa KJM-1 which was adapted to serum-free medium," Cytotechnology. 3(2):133-140.

(Continued)

*Primary Examiner* — Yong Pak
(74) *Attorney, Agent, or Firm* — Lathrop Gage LLP; James H. Velema, Esq.

(57) ABSTRACT

The present invention pertains to an isolated P450 enzyme comprising or consisting of an amino acid sequence at least 80% identical to SEQ ID NO: 1, wherein said sequence comprises a threonine at position corresponding to position 225 and/or an aspartic acid mutation at position corresponding to position 289. The invention also concerns an isolated nucleic acid comprising a sequence encoding said enzyme, a vector comprising said nucleic acid, and a host cell containing said nucleic acid or said vector. Methods for preparing said enzyme and methods for producing steroid hormone precursors using the enzyme or the host cells featured in the invention are also provided.

7 Claims, 5 Drawing Sheets

(56) References Cited

OTHER PUBLICATIONS

Miyaji et al. (1990) "Efficient expression of human beta-interferon in Namalwa KJM-1 cells adapted to serum-free medium by a dhfr gene coamplification method," Cytotechnology. 4(2):173-180.

Mizukami et al. (1987) "A new SV40-based vector developed for cDNA expression in animal cells," J. Biochem. 101(5):1307-1310.

O'Hare et al. (1981) "Transformation of mouse fibroblasts to methotrexate resistance by a recombinant plasmid expressing a prokaryotic dihydrofolate reductase," Proc. Natl. Acad. Sci. USA. 3:1527-1531.

Sagara et al. (1993) "Direct expression of adrenodoxin reductase in *Escherichia coli* and the functional characterization," Biol. Pharm. Bull. 16:627-630.

Strushkevich et al. (2005) "Role of positively charged residues Lys267, Lys270, and Arg411 of cytochrome P450scc (Cyp11A1) in interaction with adrenodoxin," Biochemistry (Moscow). 70(6):664-671.

Szczebara et al. (2003) "Total biosynthesis of hydrocortisone from a simple carbon source in yeast," Nat. Biotechnol. 21(2):143-149.

Uhlmann et al. (1992) "Expression of bovine adrenodoxin in *E. coli* and site-directed mutagenesis of /2 Fe-2S/cluster ligands," Biochem. Biophys. Res. Commun. 188:1131-1138.

Urlacher et al. (2011) "Cytochrome P450 monooxygenases: an update on perspectives for synthetic application," Trends in Biotechnology. 30(1):26-36.

Urlaub (1980) "Isolation of Chinese hamster cell mutants deficient in dihydrofolate reductase activity," Proc. Natl. Acad. Sci. USA. 77(7):4216-4220.

Van Bogaert et al. (2011) "The role of cytochrome P450 monooxygenases in microbial fatty acid metabolism," FEBS J. 278(2):206-221.

Wittchen et al. (1995) "Inactivation of the major extracellular protease from Bacillus megaterium DSM319 by gene replacement," Appl. Microbiol. Biotechnol. 42:871-877.

Woods (1998) "Expression of catalytically active human cytochrome p450scc in *Escherichia coli* and mutagenesis of isoleucine-462," Arch. Biochem. Biophys. 353(1):109-115.

International Search Report with Written Opinion corresponding to International Patent Application No. PCT/EP2015/050866, mailed May 7, 2015.

* cited by examiner

CYTOCHROME P450 POLYPEPTIDE WITH INCREASED ENZYME ACTIVITY

The present invention concerns cytochrome P450 monooxygenases with increased enzymatic activity.

Mammalian mitochondrial P450s constitute a small family of cytochromes that perform specific reactions inside mitochondria and play an important role in the metabolism of a variety of hydrophobic compounds. For example, P450c11beta and P450c11AS (encoded by the CYP11B1 and CYP11B2 genes) perform the final step of glucocorticoid and mineralocorticoid biosynthesis, respectively. P450c11beta is a classical steroid 11beta-hydroxylase that converts 11deoxycortisol into hydrocortisone, while P450c11AS catalyses the transformation of deoxycorticosterone into aldosterone in three consecutive steps. CYP27A1 is another example of an inner mitochondrial P450 which is a sterol 27-hydroxylase and vitamin D25 hydroxylase. Finally, the most emblematic mitochondrial P450 is P450scc (Side Chain Cleaving enzyme), encoded by the CYP11A1 gene, which cleaves the cholesterol side chain thus transforming cholesterol into pregnenolone by two consecutive hydroxylations and a final cleaving. P450scc performs the first key step of steroid biosynthesis by transforming a sterol into steroid.

The P450 ability to catalyze the regio-, chemo- and stereospecific oxidation of a vast number of substrates reflects their biological roles and makes them important candidates for biotechnological applications. Particularly, steroid hormones are widely used as anti-inflammatory, contraceptive and antiproliferative drugs. In mammals, the synthesis of these steroids starts with the side-chain cleaving reaction of cholesterol to pregnenolone. Pregnenolone serves as a basis for the production of further steroid hormones such as hydrocortisone and great interests are associated with its industrial large scale conversion from low-priced substrates such as cholesterol and its plant-derived analogues. However, side-chain cleaving reaction of cholesterol to pregnenolone is a limiting step in steroids overall process. In mammals, it is catalyzed by the membrane-bound CYP11A1 enzyme.

However, for multiple reasons, biotechnological and industrial use of the P450s is difficult to implement and is not satisfactory. Mitochondrial P450 use a specific chain of electron transporters made of two proteins, namely ferredoxin reductase (FdxR) and ferredoxin (Fdx1), also named adrenodoxin reductase (AdR) and adrenodoxin (Adx). In the natural situation in vivo, FdxR gains electron from NADPH and Fdx1 shuttles electron from FdxR to the mitochondrial P450. An in vitro system has been developed where FdxR is at a catalytic concentration (0.5 µM) and Fdx1 at a saturation concentration (10 µM). In order for this in vitro system to be efficient, electrons must be appropriately fluxed to the P450.

To try to overcome these difficulties, some authors fused the three peptides P450scc (or P450c11beta), Fdx1 and FdxR using variable hinge or linker sequences. Even if this triple fusion results in a functional protein, its efficacy is low compared to the "bona fide" polypeptide and it cannot be used at industrial scale. Moreover, the mitochondrial environment is difficult to mimic in a microbial recombinant system. For example, the P450scc polypeptide can be properly targeted to yeast mitochondria. However, the targeted polypeptide cannot convert sterol into pregnenolone due to absence of substrate in the mitochondria and/or to improper folding or targeting of P450scc.

Different recombinant systems are used to produce biosynthetic pregnenolone from plant sterol. For instance, a biosynthesis system was developed in the yeast *Saccharomyces cerevisiae*. In this system, P450scc is targeted outside the mitochondria at the plasma membrane together with FdxR and Fdx1, and the sterol pathway is routed to produce sterol at the membrane. Also, P450c11beta may be targeted to mitochondria together with Fdx and FdxR1 where it may convert 11-deoxycortisol into cortisol. A bioconversion system was developed in *Bacillus megaterium*. In this system, cholesterol can be converted into pregnenolone by mature forms of P450scc, Fdx1 and FdxR1. Biosynthesis remains the most attractive technology at the industrial scale since the substrate is made as a soluble molecule from a simple carbon source by the host therefore avoiding the burden of using detergents.

Recently, efforts have been made to produce new P450scc polypeptides with improved properties. For instance, a recombinant P450scc mutant bearing a K193E mutation was created. This mutant is more soluble and thus less prone to aggregation than the recombinant wild-type polypeptide. Therefore, a higher expression level is obtained with this mutant without changing its enzymatic characteristics. However, there is still a need for improved P450scc polypeptides with increased enzymatic activity allowing optimized production of steroid hormones, particularly suitable for industrial processes.

The inventors have developed a new P450scc polypeptide bearing specific mutations. This mutant shows unexpectedly an improved enzymatic activity in terms of substrate conversion into steroid hormones.

The present invention thus concerns a new isolated P450 enzyme comprising or consisting of an amino acid sequence at least 80% identical to SEQ ID NO: 1, wherein said sequence comprises a threonine at position corresponding to position 225 and/or an aspartic acid mutation at position corresponding to position 289. In some embodiments, the new P450 enzyme is at least 85%, 90%, 95%, 98% or 99% identical to SEQ ID NO:1.

The invention also concerns an isolated nucleic acid which comprises or consists of a nucleotide sequence encoding said enzyme, a vector comprising said nucleic acid which is operatively associated with expression control sequences, and a host cell containing said nucleic acid or said vector, said host cell being, for example, a microorganism.

In one embodiment, the invention provides a genetically engineered microorganism capable of converting a substrate into a steroid hormone precursor. The substrate can be, for example, a polycyclic, unsaturated mono alcohol having an aliphatic side chain, such as cholesterol, a cholesterol analogue or a cholesterol derivative. The genetically engineered microorganism comprises, for example, a nucleic acid encoding a new P450 enzyme featured in the invention, and optionally a nucleic acid sequence encoding an adrenodoxin (Adx) and/or a nucleic acid sequence encoding an adrenodoxin reductase (AdR).

In another aspect, the invention provides an in vitro method for preparing a P450 enzyme featured in the invention, said method comprising the steps of:
 a) culturing a host cell under conditions suitable to obtain expression of the P450 enzyme; and
 b) recovering the expressed enzyme.

In another embodiment, a P450 enzyme featured in the invention is used for producing a steroid hormone precursor.

The invention further relates to a method for producing a steroid hormone precursor, comprising the steps of:
 a) providing a microorganism expressing a P450 enzyme featured in the invention, b) culturing said microorganism under conditions allowing the expression of the P450 enzyme, c) contacting the microorganism culture obtained at step b) with a substrate selected from the group consisting of polycyclic and unsaturated mono alcohols having an aliphatic side chain such as cholesterol, a cholesterol analogue and a cholesterol derivative, in conditions allowing the production, by the microorganism, of a steroid hormone precursor from said substrate, and d) recovering the steroid hormone precursor produced.

The invention also pertains to a method, such as an in vitro method, for producing a steroid hormone precursor, comprising the steps of:

a) contacting a P450 enzyme featured in the invention with an isolated adrenodoxin (Adx) polypeptide, an isolated adrenodoxin reductase (AdR) polypeptide and a substrate selected from the group consisting of polycyclic and unsaturated mono alcohols having an aliphatic side chain such as cholesterol, cholesterol analogues and derivatives in conditions allowing the transformation of said substrate into a steroid hormone precursor, and b) recovering the steroid hormone precursor obtained.

Steroid hormones are widely used as anti-inflammatory, contraceptive and antiproliferative drugs. The invention is of utility to produce a steroid hormone precursor and aid the synthesis of steroid hormones for use in humans. Steroid hormone precursor, such as pregnelonone, serves as a basis for the production of further steroid hormones such as hydrocortisone and great interests are associated with its industrial large scale conversion.

DESCRIPTION OF THE INVENTION

Enzymes

By an "isolated" enzyme or polypeptide, it is intended that the enzyme or polypeptide is no longer in its natural environment within the organism in which it is originally expressed. When referring to an enzyme or polypeptide, "purified" means that the indicated molecule is present in the substantial absence of other biological macromolecules of the same type. The term "purified" as used herein means at least 75% by weight, at least 85% by weight, at least 95% by weight, or at least 98% by weight, of biological macromolecules of the same type are present.

The term "cytochrome P450 enzyme" or "P450 enzyme" refers to a monooxygenase which is capable of catalyzing certain reactions such as those reviewed in Van Bogaert et al, 2011, FEBS J. 278(2): 206-221 or in Urlacher and Girhard, 2011, Trends in Biotechnology 30(1): 26-36, or at the website dmelson.uthsc.edu/CytochromeP450.html. As an example of such a wild-type P450 enzyme, the sequence SEQ ID NO: 4 represents the mature form of *Bos taurus* CYP11A1. The complete sequence of *Bos taurus* CYP11A1 including a transit peptide is referenced as P00189 in UniProtKB/Swiss-Prot database (last sequence update: Jul. 21, 1986).

The cytochrome P450 enzymes featured in the invention may be membrane-bound (insoluble) or cytoplasmic (soluble) in their respective original hosts. For example, P450scc (SEQ ID NO:4) catalyzes the side-chain cleavage reaction of polycyclic and unsaturated mono alcohols having an aliphatic side chain such as cholesterol, cholesterol analogues and derivatives thereof into pregnenolone or other steroid hormone precursors and derivatives, as a non-limiting example.

The inventors have developed a new P450 enzyme of sequence SEQ ID NO: 1 with improved enzymatic activity. In comparison with SEQ ID NO: 4 (wild-type scc enzyme with R at position 225 and N at position 289), the amino acid sequence SEQ ID NO: 1 comprises two mutations: an arginine to threonine mutation at position corresponding to position 225 of the sequence SEQ ID NO: 4 and an asparagine to aspartic acid mutation at position corresponding to position 289 of the sequence SEQ ID NO: 4.

In a specific embodiment, the new P450 enzyme featured in the invention displays a monooxygenase activity catalyzing the transformation of cholesterol into pregnenolone. In a particular embodiment, the new P450 enzyme displays at least 80% or more, in particular at least 85%, 90%, 95%, 100%, 125%, 150%, 175%, 200%, 225%, 250%, 275%, more particularly at least 300% or more of the monooxygenase activity of the P450 enzyme of sequence SEQ ID NO: 4.

The isolated P450 enzyme featured in the invention comprises or consists of an amino acid sequence at least 80% identical to SEQ ID NO: 1, wherein said sequence comprises a threonine at position corresponding to position 225 and/or an aspartic acid at position corresponding to position 289. In some embodiments, the new P450 enzyme is at least 85%, 90%, 95%, 98% or 99% identical to SEQ ID NO:1.

Variations in amino acid sequence may be introduced by substitution, deletion or insertion of one or more codons into the nucleic acid sequence encoding the enzyme that results in a change in the amino acid sequence of the enzyme. Amino acid substitutions may be conservative or non-conservative. In some embodiments, substitutions are conservative substitutions, in which one amino acid is substituted for another amino acid with similar structural and/or chemical properties.

A "conservative amino acid substitution" is one in which an amino acid residue is substituted by another amino acid residue having a side chain R group with similar chemical properties (e.g., charge or hydrophobicity). In general, a conservative amino acid substitution will not substantially change the functional properties of a protein. Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acid substitution groups are: valine-leucine-isoleucine, phenylalanine-tyrosine, lysine-arginine, alanine-valine, glutamate-aspartate, and asparagine-glutamine.

For example, an amino acid sequence at least 80% identical to SEQ ID NO: 1 may be a polypeptide having at least one substitution at a particular amino acid residue. In some embodiments, an amino acid sequence at least 80% identical to SEQ ID NO: 1 has at least about 80%, 81%, 82%, 83%, 84%, 85%, 86%, 87%, 88%, 89%, 90%, 91%, 92%, 93%, 94%, 95%, 96%, 97%, 98%, 99% amino acid sequence identity to the sequence SEQ ID NO: 1. Amino acid sequence identity is defined as the percentage of amino acid residues in the sequence at least 80% identical to SEQ ID NO: 1 that are identical with the amino acid residues in the reference sequence SEQ ID NO: 1, after aligning the sequences and introducing gaps, if necessary, to achieve the maximum percentage of sequence identity, and not considering any conservative substitutions as part of the sequence identity. Sequence identity may be determined over the full length of the at least 80% identical sequence, the full length of the reference sequence, or both. The percentage of identity for amino acid sequences may be calculated by performing a pairwise global alignment based on the Needleman-Wunsch alignment algorithm to find the optimum alignment (including gaps) of two sequences along their entire length, for instance using Needle, and using the BLOSUM62 matrix with a gap opening penalty of 10 and a gap extension penalty of 0.5.

In the P450 enzyme comprising or consisting of an amino acid sequence at least 80% identical to SEQ ID NO: 1, the amino acid modifications as compared with SEQ ID NO: 1 are typically located at positions such that they do not significantly undermine the biological activity of the enzyme. Indeed, the cytochrome P450 amino acid sequence presenting at least 80% identical to SEQ ID NO: 1 exhibits at least the same biological activity as the polypeptide of sequence SEQ ID NO: 1.

A "same biological activity" may denote a same biological function. Therefore, a polypeptide having a same biological activity as the polypeptide of sequence SEQ ID NO: 1 may for instance be a polypeptide having monooxygenase activity. Techniques to determine the monooxygenase activity of an enzyme are well known from the skilled person. For instance, a polypeptide having a same biological activity as the polypeptide of sequence SEQ ID NO: 1 may be a polypeptide able to catalyse the side-chain cleavage reaction of polycyclic and unsaturated mono alcohols having an aliphatic side chain such as cholesterol, cholesterol analogues and derivatives to pregnenolone or other steroid hormone precursors and derivatives, as a non-limiting example. In this case, the catalysing activity of a compound can easily be evaluated in vitro (as shown in Woods, S. T., J. Sadleir, et al. (1998) "Expression of catalytically active human cytochrome p450scc in *Escherichia coli* and mutagenesis of isoleucine-462."; *Arch Biochem Biophys* 353(1): 109-15) or in vivo (as shown in Duport, C., R. Spagnoli, et al. (1998) "Self-sufficient biosynthesis of pregnenolone and progesterone in engineered yeast"; *Nat Biotechnol* 16(2): 186-9) by the person skilled in the art, for example by means of the protocol described in Example 1.

Typically, catalysing activity may be tested in an in vitro conversion assay wherein 150 mM of HEPES buffer, adjusted to pH 7.4, containing 0.05% Tween-20 and 1 mM MgCl2, may be applied as reaction buffer. 1 unit of glucose-6-phosphate dehydrogenase, with 5 mM glucose-6-phosphate as substrate, may serve as a NADPH-regenerating system. Typically, the concentrations of CYP11A1, Adx and AdR may be of 1 μM, 20 μM and 0.5 μM, or of 0.25 μM, 5 μM and 0.125 μM, respectively. 20 μM of cholesterol, dissolved in 45% 2-hydroxypropyl-β-cyclodextrin, may serve as substrate for CYP11A1. Typically, the samples are pre-warmed to 37° C. and the reaction was started by addition of NADPH to a final concentration of 100 μM. The mixtures may be incubated at 37° C. with agitation for 30 s. The reaction may be stopped by boiling the samples in water for 30 s. To allow photometric detection at 240 nm, the steroids may be converted into their 3-keto-Δ4 derivatives using a cholesterol oxidase from *Nocardia* spec. Typically, 20 μl of a cholesterol oxidase solution (5 mg cholesterol oxidase and 5 mg Na-cholate dissolved in 5 ml of 50 mM HEPES buffer pH 7, containing 0.05% Tween-20) is added to the samples. After incubation at 37° C. for 1 h, 11-deoxycorticosterone (DOC) may be added to the reaction mixtures as an internal standard, followed by a 2-times extraction with equal volumes of ethylacetate. After evaporation, the extracts may be dissolved in acetonitrile/water.

Catalysing activity may also be tested in an in vivo conversion assay wherein the conversion of 300 μM cholesterol into progesterone is typically evaluated by HPLC after 24 h. *Bacillus megaterium* may be cultivated in TB-medium containing 10 μg/ml tetracycline at 37° C. with 180 rpm shaking. Protein expression may be induced by adding 0.25 g of xylose dissolved in 1 mL water, followed by the subsequent addition of the substrate, dissolved in 2-hydroxypropyl-β-cyclodextrin.

Alignment of the sequence SEQ ID NO: 1 with an amino acid sequence at least 80% identical to SEQ ID NO: 1 may be performed. As these two sequences have a high percentage of identity, most of their amino acids are identical. Therefore, amino acid numbering may be defined for both sequences in such a way that at least 80% of the amino acids present at positions bearing the same number in both sequences are identical (by introducing gaps, if necessary, to achieve the maximum percentage of sequence identity). In this context, "a position corresponding to position X" of the sequence SEQ ID NO: 1 denotes the position bearing said number X in the sequence at least 80% identical to SEQ ID NO: 1. The sequence SEQ ID NO: 1 may therefore be taken as a "reference sequence" for the numbering of amino acid positions in an alignment with an amino acid sequence at least 80% identical to SEQ ID NO: 1, in such a way that at least 80% of the amino acids present at a "corresponding position" in both aligned sequences are identical.

In one embodiment, the isolated P450 enzyme featured in the invention comprises or consists of an amino acid sequence at least 80% identical to SEQ ID NO: 1, wherein said sequence comprises both a threonine at position corresponding to position 225 and an aspartic acid at position corresponding to position 289.

In another embodiment, the P450 enzyme featured in the invention comprises or consists of a sequence selected from the group consisting of SEQ ID NO: 1, SEQ ID NO: 2 and SEQ ID NO: 3.

In still another embodiment, the P450 enzyme featured in the invention consists of the sequence SEQ ID NO: 1.

The enzyme featured in the invention may include one or more tag(s), which may facilitate its purification. For example, the tag can be a poly-histidine (poly-His) tag.

Nucleic Acids, Vectors, Host Cells and Method of Producing the Enzyme

In one embodiment, the invention features an isolated nucleic acid which comprises or consists of a sequence encoding a P450 enzyme featured in the invention.

Isolated nucleic acids featured in the invention, also called polynucleotides, may be DNA or RNA molecules, that encode the P450 enzyme defined in the section "Enzymes", while taking into account the degeneracy of the genetic code. The isolated nucleic acids can be obtained by standard techniques well known by those skilled in the art, such as by in vitro DNA amplification or polymerisation, in vitro gene synthesis, oligonucleotide ligation, or by a combination of these techniques.

The nucleic acids featured in the invention are advantageously in isolated or purified form. The terms "purified" and "isolated" have the same meaning as defined above.

As will be understood by those of skill in the art, it may be advantageous in some instances to produce polypeptide-encoding nucleotide molecules possessing codons non-naturally occurring in the natural nucleotide molecule. For example, codons preferred by a particular prokaryotic or eukaryotic host can be selected to increase the rate of recombinant polypeptide expression.

A nucleic acid featured in this invention can also include sequences encoding tags, carrier proteins, signal peptides, or non-transcribed or translated sequences increasing expression or stability of the molecule.

The nucleic acids featured in the invention may be used to produce a recombinant P450 enzyme in a suitable expression system. The term "expression system" means a host cell and compatible vector under suitable conditions, e.g. for the expression of a protein encoded by a foreign nucleic acid carried by the vector and introduced to the host cell.

Typically, the nucleic acid may be included in any suitable vector.

Thus, in some embodiments, the invention features a vector comprising a nucleic acid as defined above operatively associated with expression control elements, and a host cell containing said nucleic acid or said vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

Any expression vector can be used, such as a plasmid, cosmid, episome, artificial chromosome, phage or a viral vector. Examples of plasmids include replicating plasmids comprising an origin of replication, or integrative plasmids, such as for instance pUC, pcDNA, pBR, and the like.

Other examples of vectors include vectors for animal cells such as pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like.

Examples of viral vectors include adenoviral, retroviral, herpes virus and AAV vectors. Recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

The expression vector may comprise a functional expression cassette, such as anexpression cassette comprising a nucleic acid sequence encoding a polypeptide featured in the invention, which is operably linked to expression control sequences.

"Expression control sequence(s)" refers to element(s) necessary for expression of a polypeptide and, optionally, for its regulation. Expression control sequence(s) may for instance include a promoter sequence, signals for initiation and termination of translation, as well as appropriate regions for regulation of translation, such as a promoter, enhancer, terminator and the like, to cause or direct expression of said polypeptide.

In one embodiment, a vector featured in the invention may also comprise a marker gene, for example a gene making it possible to select between a transformed organism and an organism which does not contain the transfected foreign DNA. A marker gene may be a gene that confers resistance to an antibiotic.

According to a specific embodiment, a vector featured in the invention may further comprise a nucleic acid sequence encoding an adrenodoxin (Adx) and/or a nucleic acid sequence encoding an adrenodoxin reductase (AdR). Adx and AdR are oxydo-reduction partners of P450 enzymes.

"AdR" refers to Adrenodoxin reductase (EC: 1.18.1.6) or Adrenodoxin-NADP+ reductase, the enzyme which is known as the first component in the mitochondrial Cytochrome P450 electron transfer system and which is involved in the biosynthesis of all steroid hormones.

In a specific embodiment, said AdR enzyme is selected from the group consisting of AR (NADPH:adrenodoxin oxidoreductase (EC=1.18.1.6) encoded by arh1 gene) from *Schizosaccharomyces pombe* or from *Saccharomyces cerevisiae* and FNR (Ferredoxin-NADP reductase (EC=1.18.1.2) encoded by fpr gene) from *Escherichia coli.*

In a specific embodiment, the AdR enzyme is AdR from *Bos taurus* (referenced as P08165 in UniProtKB/Swiss-Prot, last sequence update: Jul. 15, 1998). In another specific embodiment, the protein sequence of said AdR is SEQ ID NO: 7. In another specific embodiment, the protein sequence of said AdR is a variant of SEQ ID NO: 7, provided it retains its biological activity.

By "Adx" is meant Adrenodoxin or Ferredoxin 1, the protein which is known for its activity of transferring electrons from Adrenodoxin reductase toCYP11A1.

In a specific embodiment, said Adx protein is selected from the group consisting of Fdx from mammalian origin, Etp1fd from *Schizosaccharomyces pombe* and Yah1 from *Saccharomyces cerevisiae.*

In a specific embodiment, the Adx protein is Adx from *Bos taurus* (referenced as P00257 in UniProtKB/Swiss-Prot, last sequence update: Jul. 1, 1989). In another specific embodiment, the protein sequence of said Adx is SEQ ID NO: 8. In another specific embodiment, the protein sequence of said Adx is a variant of SEQ ID NO: 8, provided it retains its biological activity.

A vector or nucleic acid featured in the invention can be used to transform host cells according to techniques commonly known to those skilled in the art. Insertion of said vector into the host cell may be transient or stable.

The vector may also contain sequences encoding specific signals which trigger the secretion of the translated protein or its targeting to cellular compartments or organelles. These various control signals are selected according to the host cell and may be inserted into vectors which self-replicate in the host cell, or into vectors which integrate the genome of said host.

Host cells may be prokaryotic or eukaryotic, including but not limited to bacteria, yeasts, plant cells, animal cells, insect cells, and mammalian cells, including cell lines which are commercially available in some embodiments, the expression host cells are *Escherichia coli, Lactobacilli, Bacillus*, in particular *Bacillus megaterium*, probiotic bacteria, *Pichia pastoris, Saccharomyces cerevisiae*, insect cells, plant cells, COS cells and CHO cells. In one embodiment, the host cell is a prokaryotic cell, in particular a bacterial cell. In another particular embodiment, the host cell is a eukaryotic cell, such as a yeast cell such as a cell of *Saccharomyces cerevisiae.*

Common expression systems include bacterial host cells and plasmid vectors, insect host cells and Baculovirus vectors, and mammalian host cells and vectors. Specific examples include *E. coli, B. megaterium, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cells (ATCC CRL1581), mouse P3X63-Ag8.653 cells (ATCC CRL1580), CHO cells in which a dihydrofolate reductase gene (also referred to as "DHFR gene") is defective (Urlaub G et al; 1980), rat YB2/3HL.P2.G11.16Ag.20 cells (ATCC CRL1662, also referred to as "YB2/0 cell"), and the like.

In another embodiment, the invention features a cell which has been transfected, infected or transformed by a nucleic acid and/or a vector provided herein. Consequently, the present invention further concerns a host cell containing a nucleic acid and/or a vector described herein, as well as progeny and/or derivatives of such host cells. In one embodiment, the host cell is a genetically engineered microorganism.

As used herein, the "microorganism" can be an *Escherichia coli, Bacillus licheniformis, Bacillus megaterium, Bacillus subtilis, Kluyveromyces lactis, Saccharomyces cerevisiae* or *Schizosaccharomyces pombe*.

As shown in Woods, S. T., J. Sadleir, et al. (1998) (Expression of catalytically active human cytochrome p450scc in *Escherichia coli* and mutagenesis of isoleucine-462. *Arch Biochem Biophys* 353(1): 109-15), the mature form of human P450scc was expressed in *Escherichia coli* in order to provide a more convenient source of the human enzyme and to enable structure-function studies to be done using site-directed mutagenesis. This expression system enabled to produce larger quantities of active cytochrome than have previously been isolated from placental mitochondria. The expressed P450scc was purified to near homogeneity and shown to have catalytic properties comparable to the enzyme purified from the human placenta. The mature form of human adrenodoxin was also expressed in *E. coli* and supported cholesterol side chain cleavage activity with the same Vmax as that observed using bovine adrenodoxin but with a higher Km. Mutation of Ile-462 to Leu in human P450scc caused a decrease in the catalytic rate constant (kcat) with cholesterol as substrate, increased the Km for 22R-hydroxycholesterol, but did not affect the kinetic constants for 20 alpha-hydroxycholesterol.

As shown in Duport, C., R. Spagnoli, et al. (1998) (Self-sufficient biosynthesis of pregnenolone and progesterone in engineered yeast. *Nat Biotechnol* 16(2): 186-9), the first two steps of the steroidogenic pathway were reproduced in *Saccharomyces cerevisiae*. Engineering of sterol biosynthesis by disruption of the delta 22-desaturase gene and introduction of the *Arabidopsis thaliana* delta 7-reductase activity and coexpression of bovine side chain cleavage cytochrome P450, adrenodoxin, and adrenodoxin reductase, lead to pregnenolone biosynthesis from a simple carbon source. Following additional coexpression of human 3 beta-hydroxysteroid dehydrogenase/isomerase, pregnenolone was further metabolized to progesterone. Steroid formation appeared to be coupled to yeast sterol biosynthesis.

In Szczebara, F. M., C. Chandelier, et al. (2003) (Total biosynthesis of hydrocortisone from a simple carbon source in yeast; Nat Biotechnol 21(2): 143-9), the production of hydrocortisone, the major adrenal glucocorticoid of mammals and an important intermediate of steroidal drug synthesis, was reported from a simple carbon source by recombinant *Saccharomyces cerevisiae* strains. An artificial and fully self-sufficient biosynthetic pathway involving 13 engineered genes was assembled and expressed in a single yeast strain. Endogenous sterol biosynthesis was rerouted to produce compatible sterols to serve as substrates for the heterologous part of the pathway. Biosynthesis involved eight mammalian proteins (mature forms of CYP11A1, adrenodoxin (ADX), and adrenodoxin reductase (ADR); mitochondrial forms of ADX and CYP11B1; 3beta-HSD, CYP17A1, and CYP21A1). Optimization involved modulating the two mitochondrial systems and disrupting of unwanted side reactions associated with ATF2, GCY1, and YPR1 gene products. Hydrocortisone was the major steroid produced. This work demonstrated the feasibility of transfering a complex biosynthetic pathway from higher eukaryotes into microorganisms.

In a specific embodiment, the microorganism is *Bacillus megaterium*, in particular the strain referred to as *Bacillus megaterium* MS941. The expression "*Bacillus megaterium* MS941 strain" refers to the strain referenced in Wittchen and Meinhardt, 1995, Appl Microbiol Biotechnol. 42: 871-877, and derived from the DSM319 strain (Deutsche Stammsammlung von Mikroorganismen and Zellkulturen).

The system described previously using *E Coli* and the system using *B. megaterium* are two systems that are capable of realizing sterol and sterol derivatives conversion either in vitro with *E. coli* or in cellulo with *B. megaterium*. These technologies can evaluate the capacities of P450scc and substrates to function together. Both technologies require an efficient method to solubilize the substrates so that they are accessible to the enzyme. This solubilization could be challenging at the industrial level (large voume) both in financial and scientific terms.

A third organism *S. cerevisiae* is a particularly advantageous organism in this regard; its large fermentation is well mastered at cubic meter or higher levels and it has the potent capacity to produce steroids such as pregnenolone from a simple carbon source such as glucose and/or ethanol thus avoiding of detergent or solubilizing chemical such as beta-cyclodextrin (as referenced above: Duport, C., R. Spagnoli, et al. (1998); Szczebara, F. M., C. Chandelier, et al. (2003)). To permit in vivo steroid synthesis, the sterol biosynthesis was routed to produce a P450scc compatible sterol.

As *S. cerevisiae* fermentation is well mastered at large scale, introduction of the newly described P450scc cDNA into a suitable *S. cerevisiae* routed for campesterol, or other sterols described as substrates, in the presence of an appropriate electron carrier is an asset for production of steroid. This recombinant organism can be used for evaluating a new P450scc cDNA as described herein.

Therefore, in another specific embodiment, the microorganism is *Saccharomyces cerevisiae*.

The term "genetically engineered" microorganism refers to any microorganism which has been modified by genetic engineering techniques known in the field by the skilled in the art. For methods related to particular microorganisms, the person skilled in the art can referto reference manuals such as for yeast: "Methods in yeast genetics" —A laboratory course manual by M Rose, F Winston and P Hieter. pp 198. Cold Spring Harbor Laboratory Press, Cold Spring Harbor, N.Y. 1990. ISBN 0-87969-354-1.

These techniques are conventional techniques, unless otherwise indicated, in the fields of bioinformatics, cell biology, cell culture, molecular biology, transgenic biology, microbiology, recombinant DNA, and immunology, which are within the skill of the art. Such techniques are explained fully in the literature.

As used herein, "genetic engineering techniques" relate to technologies allowing the expression or overexpression of gene expression known in the field by the skilled in the art. The expression or overexpression of a gene of interest can be achieved by introducing into a cell or a microorganism an exogenous nucleic acid sequence comprising such gene of interest, by any transformation technologies known by the skilled in the art.

The term "transformation" or "transfection" means the introduction of a "foreign" (i.e. heterologous) gene, DNA or RNA sequence to a host cell, so that the host cell will express the introduced gene or sequence to produce a desired substance, typically a protein or enzyme coded by the introduced gene or sequence. The transfection of the host cell may be performed using any standard technique, such as chemical transformation, electroporation, phosphate calcium precipitation or lipofection. The transformation techniques also include for instance the PEG-mediated protoplast transformation technique (Barg et al, 2005, Microbial Processes and Products 165-184).

"Exogenous nucleic acid sequence(s)" relates to nucleic acid sequence(s) non originally and/or non naturally expressed in the considered microorganism or the way it is in the natural strain of microorganism (in term of expression level for example), and which have been used to transform said microorganism in order to obtain a genetically engineered microorganism as referred above. In a specific embodiment, the exogenous nucleic acid sequence originates from another species than the considered microorganism (e.g. another species of microorganism or organism). In another specific embodiment, exogenous sequence originates from the same microorganism.

Said exogenous nucleic acid sequence(s) may encode proteins of interest such as cytochrome P450 and oxydoreduction partners AdR and Adx and the expression "exogenous DNA" can designate each individual sequence or encompass a whole sequence comprising each individual sequence. As a non-limiting example, said exogenous nucleic acid sequences are integrated into the genome of said microorganism by techniques known in the field, such as by homologous recombination.

In one aspect, the invention provides a genetically engineered microorganism capable of converting a substrate selected from the group consisting of polycyclic and unsaturated mono alcohols having an aliphatic side chain such as cholesterol, cholesterol analogues and derivatives into a steroid hormone precursor, wherein said microorganism comprises a nucleic acid featured in the invention, and optionally an exogenous nucleic acid sequence encoding an Adx and/or an exogenous nucleic acid sequence encoding an AdR.

In a specific embodiment, the genetically engineered microorganism is *Saccharomyces cerevisiae*.

In another specific embodiment, the genetically engineered microorganism is *Bacillus megaterium*, in particular the *Bacillus megaterium* MS941 strain.

The present invention also relates to an in vitro method for preparing a P450 enzyme featured in the invention, said method comprising the steps of:
 a) culturing a host cell under conditions suitable to obtain expression of the P450 enzyme; and
 b) recovering the expressed enzyme.

"Conditions suitable to obtain expression of the P450 enzyme" are well known by the skilled in the art. Typically, either LB-(25 g/L), TB-(24 g/L yeast extract, 12 g/L tryptone, 0.4% glycerol, 10 mM potassium phosphate buffer) or EnPresso™ Tablet medium are used for the cultivation of the host cell. A pre-culture may be performed by inoculating 50 mL medium containing 10 µg/mL tetracycline with cells from a plate or glycerol stock. A main culture may then be performed by inoculating 50 mL medium containing 10 µg/mL tetracycline with 500 µL sample of the pre-culture.

The main culture is typically grown until an optical density of ~0.4 is reached. Protein expression may be induced after addition of 0.25 g xylose dissolved in 1 mL distilled water.

The P450 enzyme can then be purified by means of well-known procedures for purification: it may be purified from lysates or cell extracts, inclusion bodies or from the culture supernatant by methods such as HPLC chromatography, immunoaffinity techniques with specific antibodies, and the like.

Alternatively, the P450 enzyme may be expressed in vitro with a cell-free transcription and translation system from a DNA or RNA matrix containing required elements for its expression in a cell lysate or reconstituted system (for example, Rapid Translation System®, Roche Diagnostics or Retic Lysate IVT™, Ambion).

Methods of Producing Steroid Hormone Precursor

As shown in Examples 2-4, the inventors have developed a new P450scc enzyme bearing specific mutations which shows an improved enzymatic activity in terms of substrate conversion into steroid hormone precursor.

Therefore, in another aspect, the invention pertains to the use of a P450 enzyme featured in the invention for producing a steroid hormone precursor.

The invention further provides methods for producing a steroid hormone precursor as described below.

A first method for producing a steroid hormone precursor comprises the steps of:
 a) providing a microorganism as described above,
 b) culturing said microorganism under conditions allowing the expression of a P450 enzyme featured in the invention,
 c) contacting the microorganism culture obtained at step b) with a substrate selected from the group consisting of polycyclic and unsaturated mono alcohols having an aliphatic side chain such as cholesterol, a cholesterol analogue and a cholesterol derivative, in conditions allowing the production, by the microorganism, of a steroid hormone precursor from said substrate, and
 d) recovering the steroid hormone precursor produced.

According to a specific embodiment, steps b) and c) are performed simultaneously. In this case, the method for producing a steroid hormone precursor comprises the steps of:
 a) providing a microorganism as described above,
 b) culturing said microorganism in the presence of a substrate selected from the group consisting of polycyclic and unsaturated mono alcohols having an aliphatic side chain such as cholesterol, a cholesterol analogue and a cholesterol derivative, in conditions allowing the expression of a P450 enzyme featured in the invention and allowing the production, by the microorganism, of the steroid hormone precursor from said substrate, and
 c) recovering the steroid hormone precursor produced.

A second method for producing a steroid hormone precursor comprises the steps of:
 a) contacting a P450 enzyme featured in the invention with an isolated Adx polypeptide, an isolated AdR polypeptide and a substrate selected from the group consisting of polycyclic and unsaturated mono alcohols having an aliphatic side chain such as cholesterol, a cholesterol analogue and a cholesterol derivative in conditions allowing the transformation of said substrate into a steroid hormone precursor, and
 b) recovering the steroid hormone precursor obtained.

As used herein, the term "substrate" encompasses polycyclic and unsaturated mono alcohols having an aliphatic side chain such as phytosterol derived from cycloartenol and lanosterol. Among these substrates, "cholesterol, cholesterol analogues and derivatives thereof" refers to a list of substrates selected from the group consisting of cholesterol, brassicasterol, campesterol, ergostadienol such as ergosta 5, 22 dienol, ergosta 5, 24 (28) dienol, ergosta 5, 24(28) diene 3beta ol, ergosta 5, 24 (25) dienol, ergostatrienol such as ergosta 5, 22, 24 (25) trienol, ergosta 5, 22, 24 (28) trienol, ergosta 5, 7, 22 trienol, ergostatetrenol such as ergosta 5, 7, 22, 24 (25) ou ergosta 5, 7, 22, 24 (28), desmosterol, beta-sitosterol, generol, a mixture of oxysterols, stigmasterol, vitamin D, 7-Dehydrocholesterol and ergosterol. Sterol mixes currently used in industrial processes are also encompassed in this definition of substrates, such as generol 100 and ADM90 (comprising brassicasterol+campesterol+stigmasterol+beta-sitosterol at different ratios).

In a particular embodiment, the substrate is selected from the group consisting of cholesterol, campesterol, desmosterol and ergosta 5, 24(28) diene 3beta ol. In a specific embodiment, the substrate is ergosterol.

In a specific embodiment, the "steroid hormone precursor" is selected from the group consisting of pregnenolone, 7-Dehydropregnenolone, Hydroxyergosterol, and Hydroxystigmasterol. In another specific embodiment, said steroid hormone precursor is selected from the group of hydroxylated cholesterol analogues and secosteroids (such as vitamins D2 and D3 as derivatives of the cholesterol analogues 7-dehydrocholesterol and ergosterol). In a particular embodiment, the steroid hormone precursor is pregnenolone.

"Culturing the microorganism in the presence of a substrate" means physically interacting said microorganism with a substrate as defined above. This interaction can be achieved within a culture medium or not. In a specific embodiment, said culture medium contains agents for the permeabilization of a microorganism according to the present invention and/or the solubilization of a substrate according to the present invention. Dissolution of the substrate in these agents can be prior to the addition to microorganism culture.

"Contacting a P450 enzyme with a substrate" means physically interacting said P450 enzyme with a substrate as defined above. This interaction can be achieved within a medium or not. In a specific embodiment, said medium contains agents for the solubilization of a substrate according to the present invention. Dissolution of the substrate in these agents can be prior to the addition to said medium.

The agents used for the dissolution of the substrate can be selected from the group consisting of ethanol, Tween-80, tergitol, polyvinylpyrrolidone (PVP), saponins (such as Quillaja saponin which is contained within crude extracts of the soap bark tree Quillaja saponaria for example), cyclodextrins and derivatives thereof (e.g. 2-hydroxypropyl-β-cyclodextrin). In another specific embodiment, mixtures of these agents can be used, such as a mixture of ethanol and Tween-80, a mixture of tergitol and ethanol, a mixture of saponins (e.g. Quillaja saponin) and cyclodextrins as non-limiting examples. Cyclodextrin derivatives can be used, such as 2-hydroxypropyl-β-cyclodextrin. In another specific embodiment, substrates are co-crystallized with polyvinylpyrrolidone (PVP).

In another embodiment, substrate is first dissolved in 2-hydroxypropyl-β-cyclodextrin prior to addition to the microorganism culture wherein said culture contains Quillaja saponin. In another embodiment, substrates are dissolved in a solution comprising a percentage of 2-hydroxypropyl-β-cyclodextrin ranging from 10 to 60%, e.g., 20 to 50%, e.g., 40 to 50%, and a percentage of Quillaja saponin ranging from 1 to 10%, e.g., 2 to 8%, e.g., 3 to 6%. In another embodiment, substrates are dissolved in a solution comprising 45% of 2-hydroxypropyl-β-cyclodextrin and 4% of Quillaja saponin.

In another embodiment, the final concentration of 2-hydroxypropyl-β-cyclodextrin in the microorganism culture is between 1 and 4%, e.g., between 2 and 3%, such as 2.25% as illustrated in example 2. In another embodiment, the final concentration of Quillaja saponin in the microorganism culture is between 0.05 and 0.25%, e.g., between 0.075 and 0.225%, e.g., between 0.1 and 0.2%.

The "culturing of said microorganism under conditions allowing the expression of said exogenous nucleic acid sequences" may be performed according to any well-known culturing and inducing methods in the biotechnology field such as described in Bleif et al. (Appl Microbiol Biotechnol (2012) 93:1135-1146) or in Korneli et al. (Journal of Biotechnology 163 (2013) 87-96).

"Conditions allowing the transformation of said substrate into a steroid hormone precursor" include in vitro conditions, such as the reagents used, the reagent concentrations, the temperature, the use of agitation, the duration of the reaction or incubation, etc., which favors the transformation of said substrate into a steroid hormone precursor. These conditions may be determined and adjusted by methods known to those skilled in the art.

As a non-limiting example, the reaction may be performed in presence of glucose-6-phosphate dehydrogenase and glucose-6-phosphate, typically in 150 mM of HEPES buffer, for example adjusted to pH 7.4, containing typically 0.05% Tween-20 and 1 mM MgCl2. The concentrations of the P450 enzyme, Adx and AdR may for instance be of 1 µM, 20 µM and 0.5 µM, or of 0.25 µM, 5 µM and 0.125 µM, respectively. The polycyclic and unsaturated mono alcohols having an aliphatic side chain such as cholesterol, cholesterol analogue or cholesterol derivative may be dissolved in 45% 2-hydroxypropyl-β-cyclodextrin. The samples may be pre-warmed to 37° C. and NADPH may be added to a final concentration of 100 µM. The mixtures may be incubated at 37° C. with agitation.

In a specific embodiment, the steroid hormone precursor used in any method for producing a steroid hormone precursor is pregnenolone. As used herein, "pregnenolone" refers to a steroid hormone also referred to as 3β-hydroxy-pregn-5-en-20-one.

BRIEF DESCRIPTION OF THE SEQUENCES

SEQ ID NO: 1 shows the amino acid sequence of CYP11A1 comprising a threonine at position 225 and an aspartic acid at position 289 (polypeptide SA1).

SEQ ID NO: 2 shows the amino acid sequence of CYP11A1 comprising a threonine at position 225.

SEQ ID NO: 3 shows the amino acid sequence of CYP11A1 comprising an aspartic acid, at position 289.

SEQ ID NO: 4 shows the amino acid sequence of WT Bos taurus CYP11A1 (polypeptide SA4; WT P450scc).

SEQ ID NO: 5 shows the sequence of the plasmid pSMF2.1_CYP11A1BYM encoding for SA1 of SEQ ID NO: 1.

SEQ ID NO: 6 shows the amino acid sequence of the polypeptide SA6 (P450scc-I1A-K193E).

SEQ ID NO: 7 shows the amino acid sequence of AdR.

SEQ ID NO: 8 shows the amino acid sequence of Adx.

Figure 2:
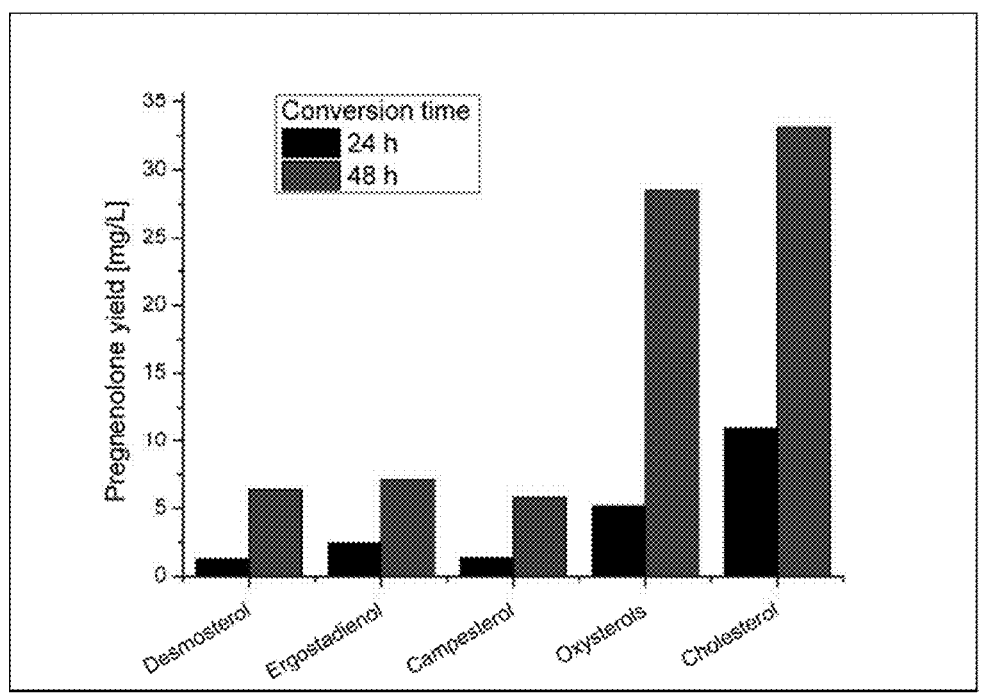

FIG. 2: Pregnelonone quantification from HPLC-chromatogram showing the in vivo conversion of different substrates into pregnenolone by the cytochrome P450 polypeptide SA1 (SEQ ID NO:1).

Figure 3:
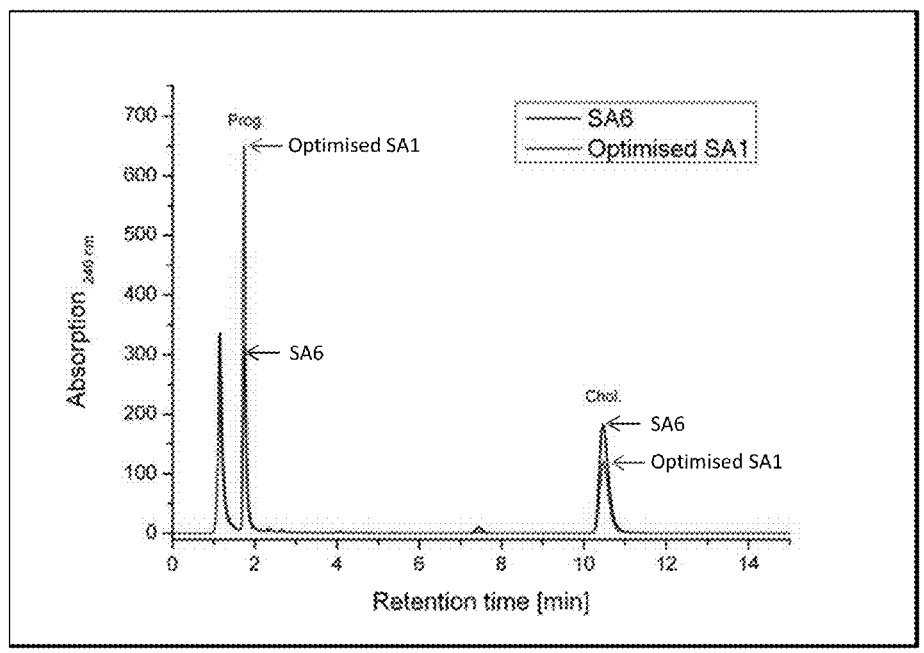

FIG. 3: HPLC-chromatogram showing the in vivo conversion of 300 µM cholesterol by the cytochrome P450 polypeptides SA1 (SEQ ID NO:1) and SA6 (control having sequence SEQ ID NO: 6) after 24 h. Legend: Chol.: cholesterol, Prog.: pregnenolone.

Figure 4:
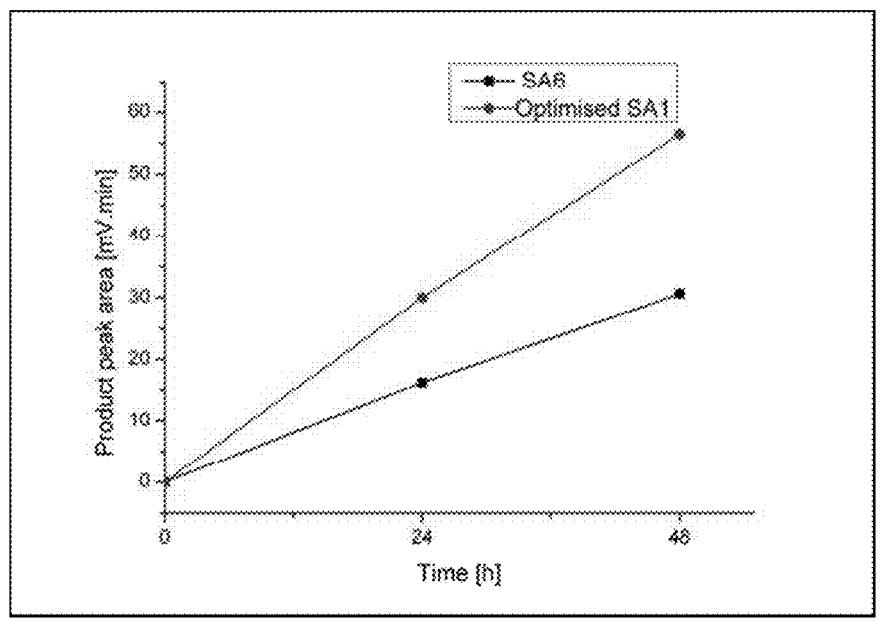

FIG. 4: Time course for the in vivo conversion of 300 µM cholesterol by the cytochrome P450 polypeptides SA1 (SEQ ID NO:1) and SA6 (control having sequence SEQ ID NO: 6).

Figure 5:
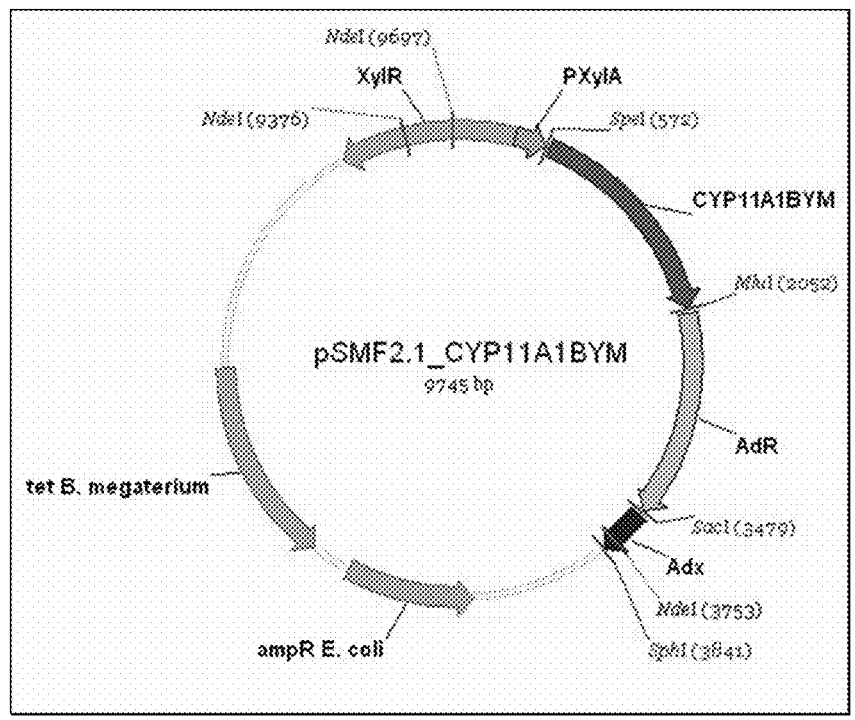

FIG. 5: Vector map of pSMF2.1_CYP11A1BYM encoding for SA1 (SEQ ID NO: 1).

EXAMPLES

Example 1

Materials and Methods

Protein Synthesis

CYP11A1 variants were obtained by gene synthesis and cloned into pTRC99A, fused to a poly-His tag. C43DE3-*E. coli* cells were co-transformed with each vector and the chaperone-encoding pGro12. The purification was performed as described in Janocha et al. (*Biochim Biophys Acta*. (2011) January;1814(1):126-31). The purity was assessed by SDS-PAGE. Concentrations of the purified proteins were determined by CO-difference spectra, after treatment with sodium dithionite and exposure to CO.

Adx and AdR were purified according to Uhlmann et al. (Biochem. Biophys. Res. Commun., 188 (1992), pp. 1131-1138) and Sagara et al. (Biol. Pharm. Bull., 16 (1993), pp. 627-630), respectively.

In Vitro Conversion Assay

For in vitro enzyme assays, 150 mM of HEPES buffer, adjusted to pH 7.4, containing 0.05% Tween-20 and 1 mM MgCl2, were applied as reaction buffer. 1 unit of glucose-6-phosphate dehydrogenase, with 5 mM glucose-6-phosphate as substrate, served as a NADPH-regenerating system.

For WT P450scc (noted "SA4", SEQ ID NO: 4) and P450scc-I1A-K193E (noted "SA6", SEQ ID NO: 6) the concentrations of CYP11A1, Adx and AdR were of 1 µM, 20 µM and 0.5 µM, and for P450scc-R225T-N289D (noted "SA1", SEQ ID NO: 1) the concentrations of CYP11A1, Adx and AdR were of 0.25 µM, 5 µM and 0.125 µM, respectively.

20 µM of cholesterol, dissolved in 45% 2-hydroxypropyl-β-cyclodextrin, served as substrate for CYP11A1.

The samples were pre-warmed to 37° C. and the reaction was started by addition of NADPH to a final concentration of 100 µM. The mixtures were incubated at 37° C. with agitation for 30 s. The reaction was stopped by boiling the samples in water for 30 s.

To allow photometric detection at 240 nm, the steroids were converted into their 3-keto-Δ4 derivatives using a cholesterol oxidase from *Nocardia* spec.

20 µl of a cholesterol oxidase solution (5 mg cholesterol oxidase and 5 mg Na-cholate dissolved in 5 ml of 50 mM HEPES buffer pH 7, containing 0.05% Tween-20) were added to the samples. After incubation at 37° C. for 1 h, 11-deoxycorticosterone (DOC) was added to the reaction mixtures as an internal standard, followed by a 2-times extraction with equal volumes of ethylacetate. After evaporation, the extracts were dissolved in acetonitrile/water.

In Vivo Conversion Assay

The in vivo conversion of 300 µM cholesterol into pregnelonone was evaluated by HPLC after 24 h. *Bacillus megaterium* was cultivated in TB-medium containing 10 µg/ml tetracycline at 37° C. with 180 rpm shaking. Protein expression was induced by adding 0.25 g of xylose dissolved in 1 mL water, followed by the subsequent addition of the substrate, dissolved in 2-hydroxypropyl-β-cyclodextrin.

Example 2

In Vitro Conversion of Cholesterol by the Cytochrome P450 Polypeptides SA1 (SEQ ID NO:1) and SA4 (WT Control, SEQ ID NO:4)

After acute evaluation of the concentration of each P450scc preparation, SA1, SA4 and SA6 were used in the following in vitro assays. Each of these isoforms was reconstituted at a concentration of 1 µM in the presence of cholesterol as a substrate (20 µM) in saturating amounts of Adx and AdR.

Figure 1:
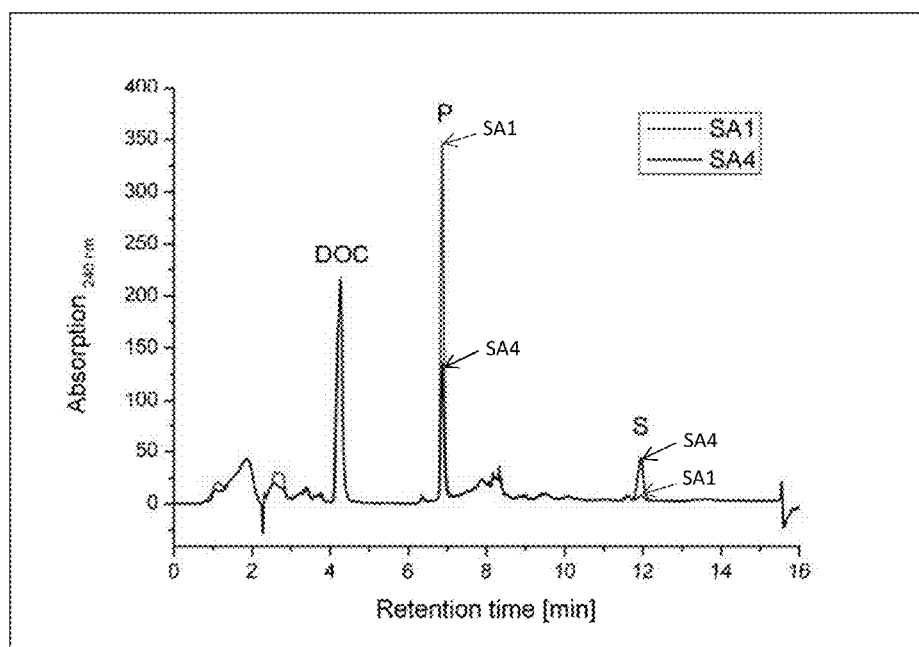
FIG. 1: HPLC-chromatogram showing the in vitro conversion of 20 µM cholesterol by the cytochrome P450 polypeptides SA1 (SEQ ID NO:1) and SA4 (control having sequence SEQ ID NO: 4). Legend: S: substrate, P: main product, DOC: 11-deoxycorticosterone.

While SA4 and SA6 showed identical activity, SA1 showed a 2-3-fold higher activity compared to SA4 and SA6 (FIG. 1). Since the substrate is already depleted after the incubation time, it is difficult to assess the differences between the SA1 and SA1/SA4 polypeptides at longer incubation time.

Example 3

In Vivo Conversion of Cholesterol by the Cytochrome P450 Polypeptides SA1 (SEQ ID NO:1) and SA6 (Control, SEQ ID NO:6)

As no measurable differences were observed between SA4 and SA6, the inventors focused their interest on comparing the SA1 and SA6 polypeptides. A new system was recently developed in which cholesterol is metabolized into pregnenolone by recombinant *Bacillus megaterium* expressing P450scc, Fdx1 and FdxR in the presence of solubilized cholesterol. SA1 and SA6 corresponding cDNAs were optimized for *Bacillus megaterium* codon BIAS and transferred into the plasmid pSFM2.1 using the appropriate restriction sites. Both PSFM2.1 plasmids bearing respectively the codon optimized SA1 and SA6 were transferred into *Bacillus megaterium* MS941 using a classical protoplast transformation protocol.

The in vivo cholesterol conversion activity was assessed after 24 h and 48 h for the SA1 and SA6 polypeptides expressed in *Bacillus megaterium*.

In accordance with the in vitro experiments, SA1 exhibited now a 2-fold higher activity compared to SA6 (FIGS. 3 and 4).

Example 4

In Vivo Conversion of Different Substrates into Pregnenolone by the Cytochrome P450 Polypeptide SA1 (SEQ ID NO:1)

Finally the improved system was used to test the SA1 polypeptide conversion capacity with various substrates of biotechnological interest: campesterol, desmosterol, ergosta-5,24(28)-dien-3β-ol and a mixture of various 20, 22-OH oxysterols.

Each substrate was converted to one main product with the same retention time as progesterone, indicating that CYP11A1 was able to cleave the side-chain of each of these substrates, yielding pregnenolone.

Pregnenolone formation was quantified for every substrate (FIG. 2). The polar oxysterols were converted at a rate comparable to cholesterol (~35 mg/L after 48 hours). Conversion of the more hydrophobic sterols campesterol, desmosterol and ergostadienol only occurred at a rate of approximately 19% after 48 hours, compared to cholesterol.

Taken together, the results show that all of the tested steroids were able to permeate through the cell membrane of *Bacillus megaterium* and were converted to pregnenolone by the CYP11A1 SA1 mutant.

The inventors thus report here a new P450scc protein, named SA1, which shows an increased conversion activity towards various sterols including cholesterol.

The invention claimed is:

1. An isolated P450 enzyme comprising an amino acid sequence at least 97% identical to SEQ ID NO: 1, wherein said sequence comprises a threonine at a position corresponding to position 225 and/or an aspartic acid at a position corresponding to position 289.

2. The enzyme according to claim 1 comprising a sequence selected from the group consisting of SEQ ID NO: 1, SEQ ID NO: 2 and SEQ ID NO: 3.

3. The enzyme according to claim 1 consisting of the sequence SEQ ID NO: 1.

4. A method for producing a steroid hormone precursor, comprising the steps of:
   a) contacting the P450 enzyme of claim 1 with an isolated adrenodoxin (Adx) polypeptide, an isolated adrenodoxin reductase (AdR) polypeptide and a substrate selected from the group consisting of polycyclic and unsaturated mono alcohols having an aliphatic side chain such as cholesterol, a cholesterol analogue and a cholesterol derivative in conditions allowing the transformation of said substrate into a steroid hormone precursor, and
   b) recovering the steroid hormone precursor.

5. The method according to claim 4, wherein the steroid hormone precursor is pregnenolone.

6. The enzyme according to claim 1, wherein said amino acid sequence is at least 98% identical to SEQ ID NO: 1.

7. The enzyme according to claim 1, wherein said amino acid sequence is at least 99% identical to SEQ ID NO: 1.

* * * * *

SEQUENCE LISTING

```
<160> NUMBER OF SEQ ID NOS: 8

<210> SEQ ID NO 1
<211> LENGTH: 481
<212> TYPE: PRT
<213> ORGANISM: Artificial Sequence
<220> FEATURE:
<223> OTHER INFORMATION: Mutated amino acid sequence of CYP11A1

<400> SEQUENCE: 1

Ile Ser Thr Lys Thr Pro Arg Pro Tyr Ser Glu Ile Pro Ser Pro Gly
1               5                   10                  15

Asp Asn Gly Trp Leu Asn Leu Tyr His Phe Trp Arg Glu Lys Gly Ser
            20                  25                  30

Gln Arg Ile His Phe Arg His Ile Glu Asn Phe Gln Lys Tyr Gly Pro
        35                  40                  45

Ile Tyr Arg Glu Lys Leu Gly Asn Leu Glu Ser Val Tyr Ile Ile His
    50                  55                  60

Pro Glu Asp Val Ala His Leu Phe Lys Phe Glu Gly Ser Tyr Pro Glu
65                  70                  75                  80

Arg Tyr Asp Ile Pro Pro Trp Leu Ala Tyr His Arg Tyr Tyr Gln Lys
                85                  90                  95

Pro Ile Gly Val Leu Phe Lys Lys Ser Gly Thr Trp Lys Lys Asp Arg
            100                 105                 110

Val Val Leu Asn Thr Glu Val Met Ala Pro Glu Ala Ile Lys Asn Phe
        115                 120                 125

Ile Pro Leu Leu Asn Pro Val Ser Gln Asp Phe Val Ser Leu Leu His
    130                 135                 140

Lys Arg Ile Lys Gln Gln Gly Ser Gly Lys Phe Val Gly Asp Ile Lys
145                 150                 155                 160

Glu Asp Leu Phe His Phe Ala Phe Glu Ser Ile Thr Asn Val Met Phe
                165                 170                 175

Gly Glu Arg Leu Gly Met Leu Glu Glu Thr Val Asn Pro Glu Ala Gln
            180                 185                 190

Lys Phe Ile Asp Ala Val Tyr Lys Met Phe His Thr Ser Val Pro Leu
        195                 200                 205

Leu Asn Val Pro Pro Glu Leu Tyr Arg Leu Phe Arg Thr Lys Thr Trp
    210                 215                 220

Thr Asp His Val Ala Ala Trp Asp Thr Ile Phe Asn Lys Ala Glu Lys
225                 230                 235                 240

Tyr Thr Glu Ile Phe Tyr Gln Asp Leu Arg Arg Lys Thr Glu Phe Arg
                245                 250                 255

Asn Tyr Pro Gly Ile Leu Tyr Cys Leu Leu Lys Ser Glu Lys Met Leu
            260                 265                 270

Leu Glu Asp Val Lys Ala Asn Ile Thr Glu Met Leu Ala Gly Gly Val
        275                 280                 285
```

```
Asp Thr Thr Ser Met Thr Leu Gln Trp His Leu Tyr Glu Met Ala Arg
    290                 295                 300

Ser Leu Asn Val Gln Glu Met Leu Arg Glu Val Leu Asn Ala Arg
305                 310                 315                 320

Arg Gln Ala Glu Gly Asp Ile Ser Lys Met Leu Gln Met Val Pro Leu
                325                 330                 335

Leu Lys Ala Ser Ile Lys Glu Thr Leu Arg Leu His Pro Ile Ser Val
                340                 345                 350

Thr Leu Gln Arg Tyr Pro Glu Ser Asp Leu Val Leu Gln Asp Tyr Leu
            355                 360                 365

Ile Pro Ala Lys Thr Leu Val Gln Val Ala Ile Tyr Ala Met Gly Arg
370                 375                 380

Asp Pro Ala Phe Phe Ser Ser Pro Asp Lys Phe Asp Pro Thr Arg Trp
385                 390                 395                 400

Leu Ser Lys Asp Lys Asp Leu Ile His Phe Arg Asn Leu Gly Phe Gly
                405                 410                 415

Trp Gly Val Arg Gln Cys Val Gly Arg Arg Ile Ala Glu Leu Glu Met
                420                 425                 430

Thr Leu Phe Leu Ile His Ile Leu Glu Asn Phe Lys Val Glu Met Gln
                435                 440                 445

His Ile Gly Asp Val Asp Thr Ile Phe Asn Leu Ile Leu Thr Pro Asp
            450                 455                 460

Lys Pro Ile Phe Leu Val Phe Arg Pro Phe Asn Gln Asp Pro Pro Gln
465                 470                 475                 480

Ala

<210> SEQ ID NO 2
<211> LENGTH: 481
<212> TYPE: PRT
<213> ORGANISM: Artificial Sequence
<220> FEATURE:
<223> OTHER INFORMATION: Mutated amino acid sequence of CYP11A1

<400> SEQUENCE: 2

Ile Ser Thr Lys Thr Pro Arg Pro Tyr Ser Glu Ile Pro Ser Pro Gly
1               5                   10                  15

Asp Asn Gly Trp Leu Asn Leu Tyr His Phe Trp Arg Glu Lys Gly Ser
                20                  25                  30

Gln Arg Ile His Phe Arg His Ile Glu Asn Phe Gln Lys Tyr Gly Pro
            35                  40                  45

Ile Tyr Arg Glu Lys Leu Gly Asn Leu Glu Ser Val Tyr Ile Ile His
50                  55                  60

Pro Glu Asp Val Ala His Leu Phe Lys Phe Glu Gly Ser Tyr Pro Glu
65                  70                  75                  80

Arg Tyr Asp Ile Pro Pro Trp Leu Ala Tyr His Arg Tyr Tyr Gln Lys
                85                  90                  95

Pro Ile Gly Val Leu Phe Lys Lys Ser Gly Thr Trp Lys Lys Asp Arg
            100                 105                 110

Val Val Leu Asn Thr Glu Val Met Ala Pro Glu Ala Ile Lys Asn Phe
        115                 120                 125

Ile Pro Leu Leu Asn Pro Val Ser Gln Asp Phe Val Ser Leu Leu His
    130                 135                 140

Lys Arg Ile Lys Gln Gln Gly Ser Gly Lys Phe Val Gly Asp Ile Lys
145                 150                 155                 160
```

```
Glu Asp Leu Phe His Phe Ala Phe Glu Ser Ile Thr Asn Val Met Phe
                165                 170                 175

Gly Glu Arg Leu Gly Met Leu Glu Glu Thr Val Asn Pro Glu Ala Gln
            180                 185                 190

Lys Phe Ile Asp Ala Val Tyr Lys Met Phe His Thr Ser Val Pro Leu
        195                 200                 205

Leu Asn Val Pro Pro Glu Leu Tyr Arg Leu Phe Arg Thr Lys Thr Trp
    210                 215                 220

Thr Asp His Val Ala Ala Trp Asp Thr Ile Phe Asn Lys Ala Glu Lys
225                 230                 235                 240

Tyr Thr Glu Ile Phe Tyr Gln Asp Leu Arg Arg Lys Thr Glu Phe Arg
                245                 250                 255

Asn Tyr Pro Gly Ile Leu Tyr Cys Leu Leu Lys Ser Glu Lys Met Leu
            260                 265                 270

Leu Glu Asp Val Lys Ala Asn Ile Thr Glu Met Leu Ala Gly Gly Val
        275                 280                 285

Asn Thr Thr Ser Met Thr Leu Gln Trp His Leu Tyr Glu Met Ala Arg
    290                 295                 300

Ser Leu Asn Val Gln Glu Met Leu Arg Glu Glu Val Leu Asn Ala Arg
305                 310                 315                 320

Arg Gln Ala Glu Gly Asp Ile Ser Lys Met Leu Gln Met Val Pro Leu
                325                 330                 335

Leu Lys Ala Ser Ile Lys Glu Thr Leu Arg Leu His Pro Ile Ser Val
            340                 345                 350

Thr Leu Gln Arg Tyr Pro Glu Ser Asp Leu Val Leu Gln Asp Tyr Leu
        355                 360                 365

Ile Pro Ala Lys Thr Leu Val Gln Val Ala Ile Tyr Ala Met Gly Arg
    370                 375                 380

Asp Pro Ala Phe Phe Ser Ser Pro Asp Lys Phe Asp Pro Thr Arg Trp
385                 390                 395                 400

Leu Ser Lys Asp Lys Asp Leu Ile His Phe Arg Asn Leu Gly Phe Gly
                405                 410                 415

Trp Gly Val Arg Gln Cys Val Gly Arg Arg Ile Ala Glu Leu Glu Met
            420                 425                 430

Thr Leu Phe Leu Ile His Ile Leu Glu Asn Phe Lys Val Glu Met Gln
        435                 440                 445

His Ile Gly Asp Val Asp Thr Ile Phe Asn Leu Ile Leu Thr Pro Asp
    450                 455                 460

Lys Pro Ile Phe Leu Val Phe Arg Pro Phe Asn Gln Asp Pro Pro Gln
465                 470                 475                 480

Ala

<210> SEQ ID NO 3
<211> LENGTH: 481
<212> TYPE: PRT
<213> ORGANISM: Artificial Sequence
<220> FEATURE:
<223> OTHER INFORMATION: Mutated amino acid sequence of CYP11A1

<400> SEQUENCE: 3

Ile Ser Thr Lys Thr Pro Arg Pro Tyr Ser Glu Ile Pro Ser Pro Gly
1               5                   10                  15

Asp Asn Gly Trp Leu Asn Leu Tyr His Phe Trp Arg Glu Lys Gly Ser
            20                  25                  30
```

```
Gln Arg Ile His Phe Arg His Ile Glu Asn Phe Gln Lys Tyr Gly Pro
         35                  40                  45

Ile Tyr Arg Glu Lys Leu Gly Asn Leu Glu Ser Val Tyr Ile Ile His
 50                  55                  60

Pro Glu Asp Val Ala His Leu Phe Lys Phe Glu Gly Ser Tyr Pro Glu
 65                  70                  75                  80

Arg Tyr Asp Ile Pro Pro Trp Leu Ala Tyr His Arg Tyr Tyr Gln Lys
                 85                  90                  95

Pro Ile Gly Val Leu Phe Lys Lys Ser Gly Thr Trp Lys Lys Asp Arg
                100                 105                 110

Val Val Leu Asn Thr Glu Val Met Ala Pro Glu Ala Ile Lys Asn Phe
            115                 120                 125

Ile Pro Leu Leu Asn Pro Val Ser Gln Asp Phe Val Ser Leu Leu His
        130                 135                 140

Lys Arg Ile Lys Gln Gln Gly Ser Gly Lys Phe Val Gly Asp Ile Lys
145                 150                 155                 160

Glu Asp Leu Phe His Phe Ala Phe Glu Ser Ile Thr Asn Val Met Phe
                165                 170                 175

Gly Glu Arg Leu Gly Met Leu Glu Thr Val Asn Pro Glu Ala Gln
            180                 185                 190

Lys Phe Ile Asp Ala Val Tyr Lys Met Phe His Thr Ser Val Pro Leu
        195                 200                 205

Leu Asn Val Pro Pro Glu Leu Tyr Arg Leu Phe Arg Thr Lys Thr Trp
    210                 215                 220

Arg Asp His Val Ala Ala Trp Asp Thr Ile Phe Asn Lys Ala Glu Lys
225                 230                 235                 240

Tyr Thr Glu Ile Phe Tyr Gln Asp Leu Arg Arg Lys Thr Glu Phe Arg
                245                 250                 255

Asn Tyr Pro Gly Ile Leu Tyr Cys Leu Leu Lys Ser Glu Lys Met Leu
            260                 265                 270

Leu Glu Asp Val Lys Ala Asn Ile Thr Glu Met Leu Ala Gly Gly Val
        275                 280                 285

Asp Thr Thr Ser Met Thr Leu Gln Trp His Leu Tyr Glu Met Ala Arg
    290                 295                 300

Ser Leu Asn Val Gln Glu Met Leu Arg Glu Glu Val Leu Asn Ala Arg
305                 310                 315                 320

Arg Gln Ala Glu Gly Asp Ile Ser Lys Met Leu Gln Met Val Pro Leu
                325                 330                 335

Leu Lys Ala Ser Ile Lys Glu Thr Leu Arg Leu His Pro Ile Ser Val
            340                 345                 350

Thr Leu Gln Arg Tyr Pro Glu Ser Asp Leu Val Leu Gln Asp Tyr Leu
        355                 360                 365

Ile Pro Ala Lys Thr Leu Val Gln Val Ala Ile Tyr Ala Met Gly Arg
        370                 375                 380

Asp Pro Ala Phe Phe Ser Ser Pro Asp Lys Phe Asp Pro Thr Arg Trp
385                 390                 395                 400

Leu Ser Lys Asp Lys Asp Leu Ile His Phe Arg Asn Leu Gly Phe Gly
                405                 410                 415

Trp Gly Val Arg Gln Cys Val Gly Arg Arg Ile Ala Glu Leu Glu Met
            420                 425                 430

Thr Leu Phe Leu Ile His Ile Leu Glu Asn Phe Lys Val Glu Met Gln
        435                 440                 445
```

```
His Ile Gly Asp Val Asp Thr Ile Phe Asn Leu Ile Leu Thr Pro Asp
    450                 455                 460
Lys Pro Ile Phe Leu Val Phe Arg Pro Phe Asn Gln Asp Pro Pro Gln
465                 470                 475                 480
Ala

<210> SEQ ID NO 4
<211> LENGTH: 481
<212> TYPE: PRT
<213> ORGANISM: Bos taurus

<400> SEQUENCE: 4

Ile Ser Thr Lys Thr Pro Arg Pro Tyr Ser Glu Ile Pro Ser Pro Gly
1               5                   10                  15

Asp Asn Gly Trp Leu Asn Leu Tyr His Phe Trp Arg Glu Lys Gly Ser
            20                  25                  30

Gln Arg Ile His Phe Arg His Ile Glu Asn Phe Gln Lys Tyr Gly Pro
        35                  40                  45

Ile Tyr Arg Glu Lys Leu Gly Asn Leu Glu Ser Val Tyr Ile Ile His
    50                  55                  60

Pro Glu Asp Val Ala His Leu Phe Lys Phe Glu Gly Ser Tyr Pro Glu
65                  70                  75                  80

Arg Tyr Asp Ile Pro Pro Trp Leu Ala Tyr His Arg Tyr Tyr Gln Lys
                85                  90                  95

Pro Ile Gly Val Leu Phe Lys Lys Ser Gly Thr Trp Lys Lys Asp Arg
            100                 105                 110

Val Val Leu Asn Thr Glu Val Met Ala Pro Glu Ala Ile Lys Asn Phe
        115                 120                 125

Ile Pro Leu Leu Asn Pro Val Ser Gln Asp Phe Val Ser Leu Leu His
    130                 135                 140

Lys Arg Ile Lys Gln Gln Gly Ser Gly Lys Phe Val Gly Asp Ile Lys
145                 150                 155                 160

Glu Asp Leu Phe His Phe Ala Phe Glu Ser Ile Thr Asn Val Met Phe
                165                 170                 175

Gly Glu Arg Leu Gly Met Leu Glu Glu Thr Val Asn Pro Glu Ala Gln
            180                 185                 190

Lys Phe Ile Asp Ala Val Tyr Lys Met Phe His Thr Ser Val Pro Leu
        195                 200                 205

Leu Asn Val Pro Pro Glu Leu Tyr Arg Leu Phe Arg Thr Lys Thr Trp
    210                 215                 220

Arg Asp His Val Ala Ala Trp Asp Thr Ile Phe Asn Lys Ala Glu Lys
225                 230                 235                 240

Tyr Thr Glu Ile Phe Tyr Gln Asp Leu Arg Arg Lys Thr Glu Phe Arg
                245                 250                 255

Asn Tyr Pro Gly Ile Leu Tyr Cys Leu Leu Lys Ser Glu Lys Met Leu
            260                 265                 270

Leu Glu Asp Val Lys Ala Asn Ile Thr Glu Met Leu Ala Gly Gly Val
        275                 280                 285

Asn Thr Thr Ser Met Thr Leu Gln Trp His Leu Tyr Glu Met Ala Arg
    290                 295                 300

Ser Leu Asn Val Gln Glu Met Leu Arg Glu Glu Val Leu Asn Ala Arg
305                 310                 315                 320

Arg Gln Ala Glu Gly Asp Ile Ser Lys Met Leu Gln Met Val Pro Leu
                325                 330                 335
```

```
Leu Lys Ala Ser Ile Lys Glu Thr Leu Arg Leu His Pro Ile Ser Val
            340                 345                 350

Thr Leu Gln Arg Tyr Pro Glu Ser Asp Leu Val Leu Gln Asp Tyr Leu
        355                 360                 365

Ile Pro Ala Lys Thr Leu Val Gln Val Ala Ile Tyr Ala Met Gly Arg
    370                 375                 380

Asp Pro Ala Phe Phe Ser Ser Pro Asp Lys Phe Asp Pro Thr Arg Trp
385                 390                 395                 400

Leu Ser Lys Asp Lys Asp Leu Ile His Phe Arg Asn Leu Gly Phe Gly
                405                 410                 415

Trp Gly Val Arg Gln Cys Val Gly Arg Arg Ile Ala Glu Leu Glu Met
            420                 425                 430

Thr Leu Phe Leu Ile His Ile Leu Glu Asn Phe Lys Val Glu Met Gln
        435                 440                 445

His Ile Gly Asp Val Asp Thr Ile Phe Asn Leu Ile Leu Thr Pro Asp
    450                 455                 460

Lys Pro Ile Phe Leu Val Phe Arg Pro Phe Asn Gln Asp Pro Pro Gln
465                 470                 475                 480

Ala

<210> SEQ ID NO 5
<211> LENGTH: 9745
<212> TYPE: DNA
<213> ORGANISM: Artificial Sequence
<220> FEATURE:
<223> OTHER INFORMATION: plasmid

<400> SEQUENCE: 5
catggtctca cttttccact ttttgtcttg tccactaaaa cccttgattt ttcatctgaa      60
taaatgctac tattaggaca cataatatta aaagaaaccc ccatctattt agttatttgt     120
ttggtcactt ataactttaa cagatgggt ttttctgtgc aaccaatttt aagggttttc     180
aatactttaa aacacataca taccaacact tcaacgcacc tttcagcaac taaaataaaa     240
atgacgttat ttctatatgt atcaagataa gaaagaacaa gttcaaaacc atcaaaaaaa     300
gacacctttt caggtgcttt ttttatttta taaactcatt ccctgatctc gacttcgttc     360
tttttttacc tctcggttat gagttagttc aaattcgttc ttttaggtt ctaaatcgtg      420 tttttcttgg aattgtgctg ttttatcctt taccttgtct acaaaccct taaaaacgtt      480 tttaaaggct tttaagccgt ctgtacgttc cttaagatca acgtgatata ggtttgctaa     540
cctttgcgtt cacttaacta acttataggg gtaacactta aaaagaatc aataacgata     600 gaaaccgctc ctaaagcagg tgcattttt cctaacgaag aaggcaatag ttcacattta      660
ttgtctaaat gagaatggac tctagaagaa acttcgtttt taatcgtatt taaaacaatg     720
ggatgagatt caattatatg atttctcaag ataacagctt ctatatcaaa tgtattaagg     780
atattggtta atccaattcc gatataaaag ccaaagtttt gaagtgcatt taacatttct     840
acatcatttt tatttgcgcg ttccacaatc tcttttcgag aaatattctt ttcttcttta     900
gagagcgaag ccagtaacgc ttttcagaa gcatataatt cccaacagcc tcgatttcca      960
cagctgcatt tgggtccatt aaaatctatc gtcatatgac ccatttcccc agaaaaaccc    1020
tgaacacctt tatacaattc gttgttaata acaagtccag ttccaattcc gatattaata    1080
ctgatgtaaa cgatgttttc atagtttttt gtcataccaa atacttttc accgtatgct      1140 cctgcattag cttcattttc aacaaaaacc ggaacattaa actcactctc aattaaaaac    1200
```

-continued

```
tgcaaatctt tgatattcca atttaagtta ggcatgaaaa taatttgctg atgacgatct   1260
acaaggcctg gaacacaaat tcctattccg actagaccat aaggggactc aggcatatgg   1320
gttacaaaac catgaataag tgcaaataaa atctctttta cttcactagc ggaagaacta   1380
gacaagtcag aagtcttctc gagaataata tttccttcta agtcggttag aattccgtta   1440
agatagtcga ctcctatatc aataccaatc gagtagcctg cattcttatt aaaaacaagc   1500
attacaggtc ttctgccgcc tctagattgc cctgccccaa tttcaaaaat aaaatctttt   1560
tcaagcagtg tatttacttg agaggagaca gtagacttgt ttaatcctgt aatctcagag   1620
agagttgccc tggagacagg ggagttcttc aaaatttcat ctaatattaa tttttgattc   1680
atttttttta ctaaagcttg atctgcaatt tgaataataa ccactccttt gtttatccac   1740
cgaactaagt tggtgttttt tgaagcttga attagatatt taaaagtatc atatctaata   1800
ttataactaa attttctaaa aaaacattg aaataaacat taaattaata tatgatggaa   1860
ttgtagttag tttacaattc caacaaacta actcaattaa gctagctgat ggataaactt   1920
gttcacttaa ttaaactagt aaatcaagga ggtgaatata caatgattag cacaaaaaca   1980
cctcgccctt attctgaaat tcctagccct ggtgataatg gatggttaaa tttatatcat   2040
ttttggcgtg aaaaaggtag ccaacgcatt cattttcgtc atattgaaaa ttttcaaaaa   2100
tatggaccta tttatcgcga aaaattagga aatttagaaa gcgtatatat tattcatcct   2160
gaagatgtag ctcatttatt taaatttgaa ggatcttatc ctgaacgcta tgatattcct   2220
ccttggcttg cttatcatcg ttattatcaa aaacctattg gcgtattatt taaaaaatct   2280
ggaacatgga aaaagatcg tgtagtatta aatacagaag taatggctcc tgaagctatt   2340
aaaaatttta ttccgttatt aaatcctgta tctcaagatt ttgtatctct tttacataaa   2400
cgtattaaac aacaaggatc tggaaaattt gttggagaca ttaaagaaga tttatttcat   2460
tttgcgtttg aatctattac aaatgttatg tttggagaac gccttggaat gttagaagaa   2520
acggtaaacc ctgaagctca aaaatttatt gatgctgtat ataaaatgtt tcatacatct   2580
gtacctttat taaacgtacc tcctgaactt tatcgtcttt ttcgaacgaa acgtggaca   2640 gatcatgtag ctgcttggga tacaatttt aataaagcgg aaaaatacac ggaaattttt   2700
tatcaagatt tacgtcgtaa aacagaattt cgtaattatc cgggaattct ttattgttta   2760
cttaaaagcg aaaagatgtt attagaagat gtaaaagcta atatcacaga atgttagca   2820 ggtggagtag atacaacaag catgacatta caatggcatc tttatgaaat ggctcgcagc   2880
ttaaacgtac aagaaatgtt acgtgaagaa gtattaaacg ctcgtcgtca agctgaaggt   2940
gatatttcta aaatgttaca aatggttcca ttattaaaag cttctattaa agaaacgtta   3000
cgtttacatc caattagcgt aacgcttcaa cgttatcctg aatctgattt agtattacaa   3060
gattatctta ttcctgctaa aacattagta caagtagcta tttatgctat gggacgtgat   3120
cctgcttttt tttcttctcc tgataaattt gatcctacac gttggttatc taaagataaa   3180
gatcttattc attttcgcaa tcttggattt ggatggggag tacgtcaatg tgtaggacgt   3240
cgtattgctg aattagaaat gacgcttttt cttattcaca ttcttgaaaa ctttaaagtg   3300
gaaatgcaac atattggaga tgtagacacg attttaact taattcttac gcctgataaa   3360 cctattttt tagtatttcg tccttttaat caagatcctc ctcaagctta ataaacgcgt   3420
ggtaccaaat caaggaggtg aatatacaat gtctacacaa gaacaaacac ctcaaatttg   3480
tgtagtagga tctggacctg ctggatttta tacagctcaa catcttttaa acatcattc   3540 tcgcgctcat gtagatattt atgaaaaaca acttgtacct tttggattag ttcgttttgg   3600
```

-continued

```
agtagctcct gatcatcctg aagtaaaaaa cgtaattaac acatttacac agacagctcg    3660
ttctgatcgt tgtgcttttt atggaaatgt agaagtagga cgtgatgtaa cagtacaaga    3720
acttcaagat gcttatcatg ctgtagtatt atcttatggt gctgaagatc atcaagcttt    3780
agatattcca ggtgaagaat tacctggtgt attttctgct cgtgcttttg taggatggta    3840
taatggatta cctgaaaatc gtgaattagc tcctgattta tcttgtgata cagctgtaat    3900
tttaggacaa ggcaacgtag ctttagatgt agctcgtatt ttattaacac ctccggatca    3960
tttagaaaaa acggatatta cagaagctgc tcttggagct ttacgtcaat ctcgtgtaaa    4020
aacagtatgg attgtaggac gtcgtggacc tttacaagta gcttttacga ttaaagaact    4080
tcgcgaaatg attcaattac ctggaacacg tcctatgtta gatcctgctg attttttagg    4140
acttcaggat cgtattaaag aagctgcacg tcctcgtaaa cgtttaatgg aattattatt    4200
acgtacagct acagaaaaac ctggtgtaga agaagctgct cgtagagcat ctgcttctcg    4260
tgcttgggga ttacgttttt ttcgtagccc tcaacaagta ttaccttctc ctgatggacg    4320
tcgtgctgct ggaattcgtt tagctgtaac acgtttagaa ggtattggag aagctacacg    4380
tgctgtacct acaggtgatg tagaagattt accttgtgga cttgtattaa gctctattgg    4440
atataaatct cgtcctattg atccttctgt accttttgat cctaaattag gtgtagtacc    4500
taatatggaa ggacgtgtag tagatgtacc tggattatat tgttctggat gggtaaaacg    4560
tggacctaca ggtgtaatta caacaacaat gacagatagc tttttaacag gccaaattct    4620
tttacaagat cttaaagctg acatttacc ttcaggacct cgtcctggat ctgcttttat    4680
taaagcttta cttgattctc gtggagtatg gcctgtatct ttttctgatt gggaaaaatt    4740
agatgctgaa gaagtatcta gaggacaagc ttctggaaaa cctcgtgaaa aattattaga    4800
tcctcaagaa atgcttcgtt tacttggcca ctaataagag ctctgtacaa atcaaggagg    4860
tgaatataca atgtcttctt ctgaagataa aataacagtc cactttataa accgtgatgg    4920
tgaaacatta acaaccaaag gaaaaattgg tgactctctg ctagatgttg tggttcaaaa    4980
taatctagat attgatggtt ttggtgcatg tgagggaacc ttggcttgtt ctacctgtca    5040
cctcatcttt gaacagcaca tatttgagaa attggaagca atcactgatg aggagaatga    5100
catgcttgat ctggcatatg gactaacaga tagatcgcgg ttgggctgcc agatctgttt    5160
gacaaaggct atggacaata tgactgttcg agtaccatag catgcgcggc cgccatgccg    5220
gctaaacctc gcgaacggat tcaccggtcc aagaattgga gctaattaat tcttgcggag    5280
aactgtgaat gcgcaaacca acccttggca gaacatatcc atcgcgtccg ccatctccag    5340
cagccgcacg cggcgcatct cgggccgcgt tgctggcgtt tttccatagg ctccgcccc    5400 ctgacgagca tcacaaaaat cgacgctcaa gtcagaggtg gcgaaacccg acaggactat    5460
aaagatacca ggcgtttccc cctggaagct ccctcgtgcg ctctcctgtt ccgaccctgc    5520
cgcttaccgg atacctgtcc gcctttctcc cttcggaag cgtggcgctt tctcatagct    5580
cacgctgtag gtatctcagt tcggtgtagg tcgttcgctc caagctgggc tgtgtgcacg    5640 aacccccccgt tcagcccgac cgctgcgcct tatccggtaa ctatcgtctt gagtccaacc    5700
cggtaagaca cgacttatcg ccactggcag cagccactgg taacaggatt agcagagcga    5760
ggtatgtagg cggtgctaca gagttcttga agtggtggcc taactacggc tacactagaa    5820
ggacagtatt tggtatctgc gctctgctga agccagttac cttcggaaaa agagttggta    5880
gctcttgatc cggcaacaa accaccgctg gtagcggtgg ttttttgtt tgcaagcagc    5940 agattacgcg cagaaaaaaa ggatctcaag aagatccttt gatcttttct acggggtctg    6000
```

-continued

```
acgctcagtg gaacgaaaac tcacgttaag ggattttggt catgagatta tcaaaaagga    6060
tcttcaccta gatccttta  aattaaaaat gaagttttaa atcaatctaa agtatatatg    6120
agtaaacttg gtctgacagt taccaatgct taatcagtga ggcacctatc tcagcgatct    6180
gtctatttcg ttcatccata gttgcctgac tccccgtcgt gtagataact acgatacggg    6240
agggcttacc atctggcccc agtgctgcaa tgataccgcg agacccacgc tcaccggctc    6300
cagatttatc agcaataaac cagccagccg aagggccga  gcgcagaagt ggtcctgcaa    6360
ctttatccgc ctccatccag tctattaatt gttgccggga agctagagta agtagttcgc    6420
cagttaatag tttgcgcaac gttgttgcca ttgctgcagg catcgtggtg tcacgctcgt    6480
cgtttggtat ggcttcattc agctccggtt cccaacgatc aaggcgagtt acatgatccc    6540
ccatgttgtg caaaaaagcg gttagctcct tcggtcctcc gatcgttgtc agaagtaagt    6600
tggccgcagt gttatcactc atggttatgg cagcactgca taattctctt actgtcatgc    6660
catccgtaag atgcttttct gtgactggtg agtactcaac caagtcattc tgagaatagt    6720
gtatgcggcg accgagttgc tcttgcccgg cgtcaacacg ggataatacc gcgccacata    6780
gcagaacttt aaaagtgctc atcattggaa aacgttcttc ggggcgaaaa ctctcaagga    6840
tcttaccgct gttgagatcc agttcgatgt aacccactcg tgcacccaac tgatcttcag    6900
catcttttac tttcaccagc gtttctgggt gagcaaaaac aggaaggcaa aatgccgcaa    6960
aaaagggaat aagggcgaca cggaaatgtt gaatactcat actcttcctt tttcaatatt    7020
attgaagcat ttatcagggt tattgtctca tgagcggata catatttgaa tgtatttaga    7080
aaaataaaca ataggggtt  ccgcgcacat ttccccgaaa agtgccacct gacgtctaag    7140
aaaccattat tatcatgaca ttaacctata aaaataggcg tatcacgagg ccctttcgtc    7200
ttcaagaatt cctgttataa aaaaaggatc aattttgaac tctctcccaa agttgatccc    7260
ttaacgattt agaaatccct ttgagaatgt ttatatacat tcaaggtaac cagccaacta    7320 atgcaatga  ttcctgaaaa aagtaataac aaattactat acagataagt tgactgatca    7380
acttccatag gtaacaacct ttgatcaagt aagggtatgg ataataaacc acctacaatt    7440
gcaatacctg ttccctctga taaaaagctg gtaaagttaa gcaaactcat tccagcacca    7500
gcttcctgct gtttcaagct acttgaaaca attgttgata taactgtttt ggtgaacgaa    7560
agcccaccta aaacaaatac gattataatt gtcatgaacc atgatgttgt ttctaaaaga    7620
aaggaagcag ttaaaaagct aacagaaaga aatgtaactc cgatgtttaa cacgtataaa    7680
ggacctcttc tatcaacaag tatcccacca atgtagccga aaataatgac actcattgtt    7740
ccagggaaaa taattacact tccgatttcg gcagtactta gctggtgaac atctttcatc    7800
atataaggaa cctagagac  aaaccctgct actgttccaa atataattcc cccacaaaga    7860
actccaatca taaaggtat  attttttccct aatccgggat caacaaaagg atctgttact    7920
ttcctgatat gttttacaaa tatcaggaat gacagcacgc taacgataag aaaagaaatg    7980
ctatatgatg ttgtaaacaa cataaaaaat acaatgccta cagacattag tataattcct    8040
ttgatatcaa aatgaccttt tatccttact tctttcttta ataatttcat aagaaacgga    8100
acagtgataa ttgttatcat aggaatgagt agaagatagg accaatgaat ataatgggct    8160
atcattccac caatcgctgg accgactcct tctcccatgg ctactatcga tccaataaga    8220
ccaaatgctt taccccctatt ttcctttgga atatagcgcg caactacaac cattacgagt    8280
gctggaaatg cagctgcacc agccccttga ataaaacgag ccataataag taaggaaaag    8340
aaagaatggc caacaaaccc aattaccgac ccgaaacaat ttattataat tccaaatagg    8400
```

```
agtaaccttt tgatgcctaa ttgatcagat agctttccat atacagctgt tccaatggaa    8460
aaggttaaca taaaggctgt gttcacccag tttgtactcg caggtggttt attaaaatca    8520
tttgcaatat caggtaatga gacgttcaaa accatttcat ttaatacgct aaaaaaagat    8580
aaaatgcaaa gccaaattaa aatttggttg tgtcgtaaat tcgattgtga ataggatgta    8640
ttcacatttc accctccaat aatgagggca gacgtagttt atagggttaa tgatacgctt    8700
ccctctttta attgaaccct gttacattca ttcacttca  taattaattc ctcctaaact    8760
tgattaaaac attttaccac atataaacta agttttaaat tcagtatttc atcacttata    8820
caacaatatg gcccgtttgt tgaactactc tttaataaaa aattttttcc gttcccaatt    8880
ccacattgca ataatagaaa atccatcttc atcggctttt tcgtcatcat ctgtatgaat    8940
caaatcgcct tcttctgtgt catcaaggtt taattttta  tgtatttctt ttaacaaacc    9000
accataggag attaaccttt tacggtgtaa accttcctcc aaatcagaca aacgtttcaa    9060 attctttttct tcatcatcgg tcataaaatc cgtatccttt acaggatatt ttgcagtttc    9120
gtcaattgcc gattgtatat ccgatttata tttattttc  ggtcgaatca tttgaacttt    9180
tacatttgga tcatagtcta atttcattgc ctttttccaa aattgaatcc attgtttttg    9240
attcacgtag ttttctgtat tcttaaaata agttggttcc acacatacca atacatgcat    9300
gtgctgatta taagaattat ctttattatt tattgtcact tccgttgcac gcataaaacc    9360
aacaagattt ttattaattt ttttatattg catcattcgg cgaaatcctt gagccatatc    9420
tgacaaactc ttatttaatt cttcgccatc ataaacattt ttaactgtta atgtgagaaa    9480
caaccaacga actgttggct tttgtttaat aacttcagca acaacctttt gtgactgaat    9540
gccatgtttc attgctctcc tccagttgca cattggacaa agcctggatt tacaaaacca    9600
cactcgatac aactttcttt cgcctgtttc acgattttgt ttatactcta atatttcagc    9660
acaatctttt actcttcag  cctttttaaa ttcaagaata tgcagaagtt caaagtaatc    9720
aacattagcg attttctttt ctctc                                          9745
```

<210> SEQ ID NO 6
<211> LENGTH: 481
<212> TYPE: PRT
<213> ORGANISM: Artificial Sequence
<220> FEATURE:
<223> OTHER INFORMATION: Mutated amino acid sequence of CYP11A1

<400> SEQUENCE: 6

```
Ala Ser Thr Lys Thr Pro Arg Pro Tyr Ser Glu Ile Pro Ser Pro Gly
1               5                   10                  15

Asp Asn Gly Trp Leu Asn Leu Tyr His Phe Trp Arg Glu Lys Gly Ser
            20                  25                  30

Gln Arg Ile His Phe Arg His Ile Glu Asn Phe Gln Lys Tyr Gly Pro
        35                  40                  45

Ile Tyr Arg Glu Lys Leu Gly Asn Leu Glu Ser Val Tyr Ile Ile His
    50                  55                  60

Pro Glu Asp Val Ala His Leu Phe Lys Phe Glu Gly Ser Tyr Pro Glu
65                  70                  75                  80

Arg Tyr Asp Ile Pro Pro Trp Leu Ala Tyr His Arg Tyr Tyr Gln Lys
                85                  90                  95

Pro Ile Gly Val Leu Phe Lys Lys Ser Gly Thr Trp Lys Lys Asp Arg
            100                 105                 110
```

Val Val Leu Asn Thr Glu Val Met Ala Pro Glu Ala Ile Lys Asn Phe
            115                 120                 125

Ile Pro Leu Leu Asn Pro Val Ser Gln Asp Phe Val Ser Leu Leu His
130                 135                 140

Lys Arg Ile Lys Gln Gln Gly Ser Gly Glu Phe Val Gly Asp Ile Lys
145                 150                 155                 160

Glu Asp Leu Phe His Phe Ala Phe Glu Ser Ile Thr Asn Val Met Phe
                165                 170                 175

Gly Glu Arg Leu Gly Met Leu Glu Glu Thr Val Asn Pro Glu Ala Gln
            180                 185                 190

Lys Phe Ile Asp Ala Val Tyr Lys Met Phe His Thr Ser Val Pro Leu
195                 200                 205

Leu Asn Val Pro Pro Glu Leu Tyr Arg Leu Phe Arg Thr Lys Thr Trp
210                 215                 220

Arg Asp His Val Ala Ala Trp Asp Thr Ile Phe Asn Lys Ala Glu Lys
225                 230                 235                 240

Tyr Thr Glu Ile Phe Tyr Gln Asp Leu Arg Arg Lys Thr Glu Phe Arg
                245                 250                 255

Asn Tyr Pro Gly Ile Leu Tyr Cys Leu Leu Lys Ser Glu Lys Met Leu
            260                 265                 270

Leu Glu Asp Val Lys Ala Asn Ile Thr Glu Met Leu Ala Gly Gly Val
275                 280                 285

Asn Thr Thr Ser Met Thr Leu Gln Trp His Leu Tyr Glu Met Ala Arg
290                 295                 300

Ser Leu Asn Val Gln Glu Met Leu Arg Glu Glu Val Leu Asn Ala Arg
305                 310                 315                 320

Arg Gln Ala Glu Gly Asp Ile Ser Lys Met Leu Gln Met Val Pro Leu
                325                 330                 335

Leu Lys Ala Ser Ile Lys Glu Thr Leu Arg Leu His Pro Ile Ser Val
            340                 345                 350

Thr Leu Gln Arg Tyr Pro Glu Ser Asp Leu Val Leu Gln Asp Tyr Leu
355                 360                 365

Ile Pro Ala Lys Thr Leu Val Gln Val Ala Ile Tyr Ala Met Gly Arg
370                 375                 380

Asp Pro Ala Phe Phe Ser Ser Pro Asp Lys Phe Asp Pro Thr Arg Trp
385                 390                 395                 400

Leu Ser Lys Asp Lys Asp Leu Ile His Phe Arg Asn Leu Gly Phe Gly
                405                 410                 415

Trp Gly Val Arg Gln Cys Val Gly Arg Arg Ile Ala Glu Leu Glu Met
            420                 425                 430

Thr Leu Phe Leu Ile His Ile Leu Glu Asn Phe Lys Val Glu Met Gln
435                 440                 445

His Ile Gly Asp Val Asp Thr Ile Phe Asn Leu Ile Leu Thr Pro Asp
450                 455                 460

Lys Pro Ile Phe Leu Val Phe Arg Pro Phe Asn Gln Asp Pro Pro Gln
465                 470                 475                 480

Ala

<210> SEQ ID NO 7
<211> LENGTH: 461
<212> TYPE: PRT
<213> ORGANISM: Bos taurus

<400> SEQUENCE: 7

```
Met Ser Thr Gln Glu Gln Thr Pro Gln Ile Cys Val Val Gly Ser Gly
1               5                   10                  15

Pro Ala Gly Phe Tyr Thr Ala Gln His Leu Leu Lys His His Ser Arg
            20                  25                  30

Ala His Val Asp Ile Tyr Glu Lys Gln Leu Val Pro Phe Gly Leu Val
        35                  40                  45

Arg Phe Gly Val Ala Pro Asp His Pro Glu Val Lys Asn Val Ile Asn
    50                  55                  60

Thr Phe Thr Gln Thr Ala Arg Ser Asp Arg Cys Ala Phe Tyr Gly Asn
65                  70                  75                  80

Val Glu Val Gly Arg Asp Val Thr Val Gln Glu Leu Gln Asp Ala Tyr
                85                  90                  95

His Ala Val Val Leu Ser Tyr Gly Ala Glu Asp His Gln Ala Leu Asp
            100                 105                 110

Ile Pro Gly Glu Glu Leu Pro Gly Val Phe Ser Ala Arg Ala Phe Val
        115                 120                 125

Gly Trp Tyr Asn Gly Leu Pro Glu Asn Arg Glu Leu Ala Pro Asp Leu
    130                 135                 140

Ser Cys Asp Thr Ala Val Ile Leu Gly Gln Gly Asn Val Ala Leu Asp
145                 150                 155                 160

Val Ala Arg Ile Leu Leu Thr Pro Pro Asp His Leu Glu Lys Thr Asp
                165                 170                 175

Ile Thr Glu Ala Ala Leu Gly Ala Leu Arg Gln Ser Arg Val Lys Thr
            180                 185                 190

Val Trp Ile Val Gly Arg Arg Gly Pro Leu Gln Val Ala Phe Thr Ile
        195                 200                 205

Lys Glu Leu Arg Glu Met Ile Gln Leu Pro Gly Thr Arg Pro Met Leu
    210                 215                 220

Asp Pro Ala Asp Phe Leu Gly Leu Gln Asp Arg Ile Lys Glu Ala Ala
225                 230                 235                 240

Arg Pro Arg Lys Arg Leu Met Glu Leu Leu Arg Thr Ala Thr Glu
                245                 250                 255

Lys Pro Gly Val Glu Ala Ala Arg Arg Ala Ser Ala Ser Arg Ala
            260                 265                 270

Trp Gly Leu Arg Phe Phe Arg Ser Pro Gln Val Leu Pro Ser Pro
        275                 280                 285

Asp Gly Arg Arg Ala Ala Gly Ile Arg Leu Ala Val Thr Arg Leu Glu
    290                 295                 300

Gly Ile Gly Glu Ala Thr Arg Ala Val Pro Thr Gly Asp Val Glu Asp
305                 310                 315                 320

Leu Pro Cys Gly Leu Val Leu Ser Ser Ile Gly Tyr Lys Ser Arg Pro
                325                 330                 335

Ile Asp Pro Ser Val Pro Phe Asp Pro Lys Leu Gly Val Val Pro Asn
            340                 345                 350

Met Glu Gly Arg Val Val Asp Val Pro Gly Leu Tyr Cys Ser Gly Trp
        355                 360                 365

Val Lys Arg Gly Pro Thr Gly Val Ile Thr Thr Thr Met Thr Asp Ser
    370                 375                 380

Phe Leu Thr Gly Gln Ile Leu Leu Gln Asp Leu Lys Ala Gly His Leu
385                 390                 395                 400

Pro Ser Gly Pro Arg Pro Gly Ser Ala Phe Ile Lys Ala Leu Leu Asp
                405                 410                 415
```

```
Ser Arg Gly Val Trp Pro Val Ser Phe Ser Asp Trp Glu Lys Leu Asp
            420             425             430

Ala Glu Glu Val Ser Arg Gly Gln Ala Ser Gly Lys Pro Arg Glu Lys
            435             440             445

Leu Leu Asp Pro Gln Glu Met Leu Arg Leu Leu Gly His
        450             455             460

<210> SEQ ID NO 8
<211> LENGTH: 109
<212> TYPE: PRT
<213> ORGANISM: Bos taurus

<400> SEQUENCE: 8

Met Ser Ser Ser Glu Asp Lys Ile Thr Val His Phe Ile Asn Arg Asp
1               5                   10                  15

Gly Glu Thr Leu Thr Thr Lys Gly Lys Ile Gly Asp Ser Leu Leu Asp
            20                  25                  30

Val Val Val Gln Asn Asn Leu Asp Ile Asp Gly Phe Gly Ala Cys Glu
        35                  40                  45

Gly Thr Leu Ala Cys Ser Thr Cys His Leu Ile Phe Glu Gln His Ile
    50                  55                  60

Phe Glu Lys Leu Glu Ala Ile Thr Asp Glu Glu Asn Asp Met Leu Asp
65                  70                  75                  80

Leu Ala Tyr Gly Leu Thr Asp Arg Ser Arg Leu Gly Cys Gln Ile Cys
                85                  90                  95

Leu Thr Lys Ala Met Asp Asn Met Thr Val Arg Val Pro
            100                 105
```